US008802853B2

(12) United States Patent
Bonk et al.

(10) Patent No.: US 8,802,853 B2
(45) Date of Patent: Aug. 12, 2014

(54) ARYLALKENYL AND ARYLALKYNYL SUBSTITUTED IMIDAZOQUINOLINES

(75) Inventors: Jason D. Bonk, Hudson, WI (US); Joseph F. Dellaria, Jr., Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 2006 days.

(21) Appl. No.: 10/596,890

(22) PCT Filed: Dec. 17, 2004

(86) PCT No.: PCT/US2004/042556
§ 371 (c)(1),
(2), (4) Date: Jun. 28, 2006

(87) PCT Pub. No.: WO2005/066170
PCT Pub. Date: Jul. 21, 2005

(65) Prior Publication Data
US 2009/0030030 A1   Jan. 29, 2009

Related U.S. Application Data

(60) Provisional application No. 60/532,982, filed on Dec. 29, 2003.

(51) Int. Cl.
*C07D 487/04* (2006.01)
*C07D 487/06* (2006.01)
*A61K 31/4375* (2006.01)

(52) U.S. Cl.
USPC .............................. 546/80; 514/290

(58) Field of Classification Search
USPC .............................. 546/80; 514/290
See application file for complete search history.

(56) References Cited

U.S. PATENT DOCUMENTS

| | | | |
|---|---|---|---|
| 3,314,941 A | 4/1967 | Littell et al. |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gester |
| 5,274,113 A | 12/1993 | Kang et al. |
| 5,342,784 A | 8/1994 | Yamada et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom |

(Continued)

FOREIGN PATENT DOCUMENTS

| AU | 2004220534 A1 | 9/2004 |
|---|---|---|
| AU | 2004229478 A1 | 10/2004 |

(Continued)

OTHER PUBLICATIONS

Dorwald F. A. Side Reactions in Organic Synthesis, 2005, Wiley: VCH, Weinheim p. IX of Preface.*
Wermuth C. Molecular variations based on Isosteric Replacements, 1996.*
Wozniak et al, "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates.", *Biotechniques*, Jun./Jul., 78, 1983.
Testerman et al, "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem*, 15, pp. 1278-1284 (1950).

(Continued)

Primary Examiner — Rita Desai

(57) ABSTRACT

Arylalkenyl and aryalkynyl substituted imidazoquinoline compounds, pharmaceutical compositions containing the compounds, intermediates, and methods of use of these compounds as immunomodulators, for inducing cytokine biosynthesis in animals and in the treatment of diseases including viral, and neoplastic, are disclosed.

15 Claims, No Drawings

(56) References Cited

U.S. PATENT DOCUMENTS

| | | |
|---|---|---|
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |
| 7,098,221 B2 | 8/2006 | Heppner et al. |

(56) References Cited

U.S. PATENT DOCUMENTS

| | | |
|---|---|---|
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1* | 11/2003 | Heppner et al. ............... 514/292 |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |

(56) References Cited

U.S. PATENT DOCUMENTS

| | | |
|---|---|---|
| 2009/0253695 A1 | 10/2009 | Kshirsagar et al. |
| 2009/0270443 A1 | 10/2009 | Stoermer et al. |
| 2009/0318435 A1 | 12/2009 | Hays et al. |
| 2010/0113565 A1 | 5/2010 | Gorden et al. |

FOREIGN PATENT DOCUMENTS

| | | | |
|---|---|---|---|
| AU | 2004264336 A1 | 2/2005 | |
| AU | 2004268625 A1 | 3/2005 | |
| AU | 2002239547 B2 | 11/2006 | |
| CA | 2044087 A1 | 12/1991 | |
| CA | 2158996 A1 | 10/1994 | |
| CN | 1354663 A | 6/2002 | |
| EP | 0 145 340 A2 | 6/1985 | |
| EP | 0 223 420 A1 | 5/1987 | |
| EP | 0 310 950 A1 | 4/1989 | |
| EP | 0 385 630 A2 | 9/1990 | |
| EP | 0 389 302 A1 | 9/1990 | |
| EP | 0 394 026 | 10/1990 | |
| EP | 0 425 306 A2 | 5/1991 | |
| EP | 0 510 260 A2 | 10/1992 | |
| EP | 0 645 389 A1 | 3/1995 | |
| EP | 0 778 277 A1 | 6/1997 | |
| EP | 0 894 797 A1 | 2/1999 | |
| EP | 1 082 960 A2 | 3/2001 | |
| EP | 1 097 709 A2 | 5/2001 | |
| EP | 1 104 764 | 6/2001 | |
| EP | 1 145 340 A2 | 10/2001 | |
| EP | 1 256 582 A1 | 11/2002 | |
| EP | 1 341 791 A2 | 9/2003 | |
| EP | 1 495 758 A2 | 1/2005 | |
| HU | 34479 A2 | 3/1985 | |
| HU | 210051 A2 | 6/1991 | |
| HU | 218950 A2 | 9/1995 | |
| IL | 73534 A | 12/1990 | |
| JP | 53050197 A | 5/1978 | |
| JP | 63010787 A | 1/1988 | |
| JP | 4066571 A | 3/1992 | |
| JP | 4327587 A | 11/1992 | |
| JP | 5286973 A | 11/1993 | |
| JP | 9-208584 | 8/1997 | |
| JP | 11-080156 A | 3/1999 | |
| JP | 11-222432 | 8/1999 | |
| JP | 2000-247884 | 9/2000 | |
| NZ | 545412 A | 12/2008 | |
| RU | 2076105 C1 | 3/1997 | |
| RU | 2127273 C1 | 3/1999 | |
| RU | 2221798 C2 | 1/2004 | |
| WO | WO-91/06682 A1 | 5/1991 | |
| WO | WO-92/06093 A1 | 4/1992 | |
| WO | WO-92/15581 A1 | 9/1992 | |
| WO | WO-92/15582 A1 | 9/1992 | |
| WO | WO-93/05042 A1 | 3/1993 | |
| WO | WO-93/09119 A1 | 5/1993 | |
| WO | WO-93/20847 A1 | 10/1993 | |
| WO | WO-94/10171 A1 | 5/1994 | |
| WO | WO-95/02597 A1 | 1/1995 | |
| WO | WO-95/02598 A1 | 1/1995 | |
| WO | WO-96/11199 A1 | 4/1996 | |
| WO | WO-96/21663 A1 | 7/1996 | |
| WO | WO-97/48703 A1 | 12/1997 | |
| WO | WO-97/48704 A1 | 12/1997 | |
| WO | WO-98/17279 A1 | 4/1998 | |
| WO | WO-98/30562 A1 | 7/1998 | |
| WO | WO-98/48805 A1 | 11/1998 | |
| WO | WO-98/50547 A2 | 11/1998 | |
| WO | WO-98/54226 A1 | 12/1998 | |
| WO | WO-99/18105 A1 | 4/1999 | |
| WO | WO-99/29693 A1 | 6/1999 | |
| WO | WO-00/06577 A1 | 2/2000 | |
| WO | WO-00/09506 A1 | 2/2000 | |
| WO | WO-00/19987 A1 | 4/2000 | |
| WO | WO-00/40228 A2 | 7/2000 | |
| WO | WO-00/47719 A2 | 8/2000 | |
| WO | WO-00/75304 A1 | 12/2000 | |
| WO | WO-00/76505 A1 | 12/2000 | |
| WO | WO-00/76518 A1 | 12/2000 | |
| WO | WO-00/76519 A1 | 12/2000 | |
| WO | WO-01/34709 A1 | 5/2001 | |
| WO | WO-01/51486 A2 | 7/2001 | |
| WO | WO-01/55439 A1 | 8/2001 | |
| WO | WO-01/58900 A1 | 8/2001 | |
| WO | WO-01/74343 A2 | 10/2001 | |
| WO | WO-01/74821 A1 | 10/2001 | |
| WO | WO-02/07725 A1 | 1/2002 | |
| WO | WO-02/22809 A2 | 3/2002 | |
| WO | WO-02/24225 A1 | 3/2002 | |
| WO | WO 02/36592 | 5/2002 | |
| WO | 0246189 | * | 6/2002 |
| WO | WO-02/46188 A2 | 6/2002 | |
| WO | WO-02/46189 A2 | 6/2002 | |
| WO | WO-02/46190 A2 | 6/2002 | |
| WO | WO-02/46191 A2 | 6/2002 | |
| WO | WO-02/46192 A2 | 6/2002 | |
| WO | WO-02/46193 A2 | 6/2002 | |
| WO | WO-02/46194 A2 | 6/2002 | |
| WO | WO-02/46749 A2 | 6/2002 | |
| WO | WO-02/085905 A1 | 10/2002 | |
| WO | WO-02/102377 A1 | 12/2002 | |
| WO | WO-03/008421 A1 | 1/2003 | |
| WO | WO-03/009852 A1 | 2/2003 | |
| WO | WO-03/020889 A2 | 3/2003 | |
| WO | WO-03/043572 A2 | 5/2003 | |
| WO | WO-03/045391 A1 | 6/2003 | |
| WO | WO-03/045494 A2 | 6/2003 | |
| WO | WO-03/045929 A1 | 6/2003 | |
| WO | WO-03/050117 A1 | 6/2003 | |
| WO | WO-03/050118 A1 | 6/2003 | |
| WO | WO-03/050119 A2 | 6/2003 | |
| WO | WO-03/050121 A1 | 6/2003 | |
| WO | WO-03/077944 A1 | 9/2003 | |
| WO | WO-03/080114 A2 | 10/2003 | |
| WO | WO-03/086280 A2 | 10/2003 | |
| WO | WO-03/086350 A1 | 10/2003 | |
| WO | WO-03/089602 A2 | 10/2003 | |
| WO | WO-03/097641 A2 | 11/2003 | |
| WO | WO-03/101949 A2 | 12/2003 | |
| WO | WO-03/103584 A2 | 12/2003 | |
| WO | WO-2004/028539 A2 | 4/2004 | |
| WO | WO-2004/041285 A1 | 5/2004 | |
| WO | WO-2004/043913 A2 | 5/2004 | |
| WO | WO-2004/053057 A2 | 6/2004 | |
| WO | WO-2004/053452 A2 | 6/2004 | |
| WO | WO-2004/058759 A1 | 7/2004 | |
| WO | WO-2004/071459 A2 | 8/2004 | |
| WO | WO-2004/075865 A2 | 9/2004 | |
| WO | WO-2004/080398 A2 | 9/2004 | |
| WO | WO-2004/091500 A2 | 10/2004 | |
| WO | WO-2004/096144 A2 | 11/2004 | |
| WO | WO-2004/110991 A2 | 12/2004 | |
| WO | WO-2004/110992 A2 | 12/2004 | |
| WO | WO-2005/003064 A2 | 1/2005 | |
| WO | WO-2005/003065 A2 | 1/2005 | |
| WO | WO-2005/016273 A2 | 2/2005 | |
| WO | WO-2005/016275 A2 | 2/2005 | |
| WO | WO 2005/018551 | 3/2005 | |
| WO | WO 2005/018555 | 3/2005 | |
| WO | WO 2005/018556 | 3/2005 | |
| WO | WO 2005/020999 | 3/2005 | |
| WO | WO-2005/023190 A2 | 3/2005 | |
| WO | WO-2005/025614 A2 | 3/2005 | |
| WO | WO-2005/029037 A2 | 3/2005 | |
| WO | WO 2005/032484 | 4/2005 | |
| WO | WO-2005/041891 A2 | 5/2005 | |
| WO | WO 2005/048933 | 6/2005 | |
| WO | WO 2005/048945 | 6/2005 | |
| WO | WO-2005/049076 A1 | 6/2005 | |
| WO | WO 2005/051317 | 6/2005 | |
| WO | WO 2005/051324 | 6/2005 | |
| WO | WO 2005/054237 | 6/2005 | |
| WO | WO 2005/054238 | 6/2005 | |
| WO | WO-2005/065678 A1 | 7/2005 | |
| WO | WO 2005/066169 | 7/2005 | |

(56) References Cited

FOREIGN PATENT DOCUMENTS

| | | |
|---|---|---|
| WO | WO 2005/066170 | 7/2005 |
| WO | WO 2005/066172 | 7/2005 |
| WO | WO-2005/067500 A2 | 7/2005 |
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO-2006/093514 A2 | 9/2006 |
| WO | WO 2006/098852 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Jain et al., "Chemical and Pharmacological Investigations of Some ψ-Substituted Alkylamino-3-aminopyridines." *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-as-triazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Wermuth at al., "Molecular Variations Based on Isosteric Replacements." The Practice of Medicinal Chemistry, pp. 203-237 (1996).

International Search Report and Written Opinion for PCT/US2004/042556 mailed Jun. 17, 2005.

International Preliminary Report on Patentability for PCT/US2004/042556 mailed Jul. 3, 2006.

[No Author Listed] "Comparative Tests." Filed Apr. 8, 2005 during prosecution for EP 00938205.2, EP 00950215.4 and EP 00938211.0 in the name of 3M Innovative Properties Co.

[No Author Listed] Chemical Abstracts. 1964;61(1):6060g.

[No Author Listed] Encyclopedia of Pharmaceutical Technology. 2nd Ed. Marcel Dekker, Inc. 2002:856-60.

Agrawal et al., Synthetic agonists of Toll-like receptors 7, 8 and 9. Biochem Soc Trans. Dec. 2007;35(Pt 6):1461-7.

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Recognition of pathogen-associated molecular patterns by TLR family. Immunol Lett. 2003;85:85-95.

Akira et al., Toll-like receptors: critical proteins linking innate and acquired immunity. Nature Immunol. 2001;2(8):675-80.

Alexopoulou et al., Recognition of double-stranded RNA and activation of NF-kappaB by Toll-like receptor 3. Nature. Oct. 18, 2001;413(6857):732-8.

Assuma et al., IL-1 and TNF Antagonists Inhibit the Inflammatory Response and Bone Loss in Experimental Periodontitis. J Immunol. 2000;160:403-09.

Au et al., Virus-mediated induction of interferon A gene requires cooperation between multiple binding factors in the interferon alpha promoter region. J Biol Chem. Nov. 15, 1993;268(32):24032-40.

Auerbach et al., Erythema nodosum following a jellyfish sting. J Emerg Med. Nov.-Dec. 1987;5(6):487-91.

Auwers, [Uber die Isomerie-Verhaltnisse in der Pyrazol-Reihe. Berichte. VI.] 1926;601-607. German.

Baffis of al., Use of interferon for prevention of hepatocellular carcinoma in cirrhotic patients with hepatitis B or hepatitis C virus infection. Ann Intern Med. Nov. 2, 1999;131(9):696-701.

Baker et al., Oral infection with Porphyromonas gingivalis and induced alveolar bone loss in immunocompetent and severe combined immunodeficient mice. Arch Oral Biol. Dec. 1994;39(12):1035-40.

Baldwin et al., Amino Acid Synthesis *via* Ring Opening of N-Sulphonyl Aziridine-2-Carboxylate Esters with Organometallic Reagents. Tetrahedron. 1993;49:6309-30.

Bártová et al., Th1 and Th2 cytokine profile in patients with early onset periodontitis and their healthy siblings. Mediators Inflamm. 2000;9(2):115-20.

Beck of al., Dental Infections and Atherosclerosis. Am Heart J. 1999;13:528-33.

Beckett et al., Configurational Studies in Synthetic Analgesics: the Synthesis of (−)- Methadone from D-(−)- Alanine. J Chem Soc. 1957;1:858-61.

Beilman et al., Experimental brown spider bite in the guinea pig: Results of treatment with dapsone or hyperbaric oxygen. J Wilderness Medicine. 1994;5:287-94.

Belikov, Abbreviated Guide to Synthetic and Natural Medications. Pharmaceutical Chemistry. Higher School. 1993;1:43-47. Russian.

Beltrami et al., Some Methylhydrazonium Salts; An Improved Synthesis of Tetramethylhydrazine. J Am Chem Soc. 1956;78:2467-68.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

(56) References Cited

OTHER PUBLICATIONS

Bertino et al., Principles of Cancer Therapy. Cecil Textbook of Medicine. Goldman et al., eds. 21th Ed. W.B. Saunders Company. 2000:1:1060-74.

Beutler et al., Tumor necrosis factor in the pathogenesis of infectious diseases. Crit Care Med. Oct. 1993;21(10 Suppl):S423-35.

Beutner et al., Therapeutic response of basal cell carcinoma to the immune response modifier imiquimod 5% cream. J Am Acad Dermatol. Dec. 1999;41(6):1002-7.

Beutner et al., Treatment of genital warts with an immune-response modifier (imiquimod). J Am Acad Dermatol. Feb. 1998;38(2 Pt 1):230-9.

Binder, Acute arthropod envenomation. Incidence, clinical features and management. Med Toxicol Adverse Drug Exp. May-Jun. 1989;4(3):163-73.

Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and *Borrelia burgdorferi* outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996; 105(5): 589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25):4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel of al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3+2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

(56) References Cited

OTHER PUBLICATIONS

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-9. Epub Jun. 26, 2003.

Hayes et at., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

(56) References Cited

OTHER PUBLICATIONS

Keating et al., Long-term follow-up of patients with chronic lymphocytic leukemia treated with fludarabine as a single agent. Blood. Jun. 1, 1993;81(11):2878-84.
Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò-nitrokenes. J Am Chem Soc. 1947;69:2271-2275.
Kornman, Host modulation as a therapeutic strategy in the treatment of periodontal disease. Clin Infect Dis. Mar. 1999;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and anti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.
Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999; 82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of yē cells and (β-chemokines in mucosal protection against SIV infection. Immunology Lett. 1999;69:25-192. Abstract 2.1.
Levy of al., Unique efficacy of Toll-like receptor 8 agonists in activating human neonatal antigen-presenting cells. Blood. Aug. 15, 2006;108(4):1284-90. Epub Apr. 25, 2006.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002;67(15):5394-7.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of *Lactococcus lactis*. Immunology Lett. 1999:69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Macchia et al., Synthesis and antiviral properties of 9-[(2-methyleneaminoxyethoxy)methyl]guanine derivatives as novel Acyclovir analogues. Farmaco. Feb. 2000;55(2):104-8.
Majeski et al., Action of venom from the brown recluse spider (*Loxosceles reclusa*) on human neutrophils. Toxicon. 1977;15(5):423-7.
Makarenkova et al., Identification of delta- and mu-type opioid receptors on human and murine dendritic cells. J Neuroimmunol. 2001;117:68-77.
Male et al., Introduction to the Immune System. In: Immunology. Elsevier. 2006:6-7.
Masihi, Progress on novel immunomodulatory agents for HIV-1 infection and other infectious diseases. Expert Opin Ther Patents. 2003;13(6):867-82.
Masiukiewicz et al., Scalable Syntheses of $N^{\alpha}$-Benzyloxycarbonyl-$_L$-Ornithine and of $N^{\alpha}$-(9-Fluorenylmethoxy)Carbonyl-$_L$-Ornithine. Org Prep Proced Int. 2002;34:531-37.
Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al, Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al, A Convenient Reduction of Amino Acids and Their Derivatives. J Org Chem. 1993;58:3568-71.
McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider: Review of Mechanism and Treatment.Options. Am J Ther. Oct. 1996;3(10):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C-N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.
Muller et al., An improved one-pot procedure for the synthesis of alkynes from aldehydes. Synlett. 1996;6:521-522.
Mutschler et al., 9.2 Anti-infectives. In: Drug Actions: Basic Principles and Therapeutic Aspects. 1995:515-80.

(56) References Cited

OTHER PUBLICATIONS

Muzio et al., Differential expression and regulation of toll-like receptors (TLR) in human leukocytes: selective expression of TLR3 in dendritic cells. J Immunol. Jun. 1, 2000;164(11):5998-6004.
Nagarajan et al., Condensed heterotricycles: synthesis of pyrazolo[3,4-c]quinoline derivatives. Indian Journal of Chemistry. 1992;31B:316-321.
Nagase et al, Expression and function of Toll-like receptors in eosinophils: activation by Toll-like receptor 7 ligand. J Immunol. Oct. 15, 2003;171(8):3977-82.
Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.
Ohana et al., Differential effect of adenosine on tumor and normal cell growth: focus on the A3 adenosine receptor. Journal of Cellular Physiology. Jan. 2001;186(1):19-23. Review.
O'Mahony et al., New patient-applied therapy for anogenital warts is rated favourably by patients. Intl J STD & AIDS. 2001;12:565-70.
Osol et al., Chapter 27: Structure-Activtiy Relationship and Drug Design. In: Remington's Pharmaceutical Sciences. 16th Ed. Mach Publishing. 1980:420-35.
Ottonello et al., Sulphonamides as anti-inflammatory agents: old drugs for new therapeutic strategies in neutrophilic inflammation? Clin Sci (Lond). Mar. 1995;88(3):331-6.
Ozinsky et al., The repertoire for pattern recognition of pathogens by the innate immune system is defined by cooperation between Toll-like receptors. Proc. Nat. Acad. Sci. 2000; 97(25):13766-71.
Page et al., Advances in the pathogenesis of periodontitis: summary of developments, clinical implications and future directions. Periodontol 2000. Jun. 1997;14:216-48.
Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.
Park et al., Sodium Dithionite Reduction of Nitroarenes Using Viologen as an Electron Phase-Transfer Catalyst. Tetrahedron Lett. 1993;34(46):7445-46.
Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.
Patrick et al., Paragraph 10.3: Drug optimization: strategies in drug design. In: An Introduction to Medicinal Chemistry. Oxford: Oxford University Press. Jan. 2005. 200-218.
Pavletic et al., Outcome of allogeneic stem cell transplantation for B cell chronic lymphocytic leukemia. Bone Marrow Transplant. Apr. 2000;25(7):717-22.
Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.
Payvandi et al., Exogenous and Endogenous IL-10 Regulate IFN-α Production by Peripheral Blood Mononuclear Cells in Response to Viral Stimulation. J Immunol. 1998;160:5861-68.
Peschke et al., Synthesis and in vitro characterization of new growth hormone secretagogues derived from ipamorelin with dipeptidomimetic N-terminals. Eur J Med Chem. 1999;34:363-380.
Peterson et al., The opioid-cytokine connection. J Neuroimmunol. 1998;83:63-69.
Phillips et al., Therapy of brown spider envenomation: a controlled trial of hyperbaric oxygen, dapsone, and cyproheptadine. Ann Emerg Med. Mar. 1995;25(3):363-8.
Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.
Powell et al., Compendium of excipients for parenteral formulations. PDA J Pharm Sci Technol. Sep.-Oct. 1998;52(5):238-311.
Prelog et al., Cycloalkeno-pyridine. Helv Chem Acta. 1945;28:1684-93. German.
Rees et al., Brown recluse spider bites. A comparison of early surgical excision versus dapsone and delayed surgical excision. Ann Surg. Nov. 1985;202(5):659-63.
Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.
Rhodes, Discovery of immunopotentiatory drugs: current and future strategies. Clin Exp Immunol. Dec. 2002;130(3):363-9.
Ribera et al., "Spontaneous" complete remissions in chronic lymphocytic leukemia: report of three cases and review of the literature. Blood Cells. 1987;12(2):471-79.
Ritter et al., A new reaction of nitriles; amides from alkenes and mononitriles. J Am Chem Soc. Dec. 1948;70(12):4045-8.
Rocca et al., Carbolines. Part VII. Ansidines, Convenient tools to synthesize fficien-β-carbolines. J Heterocyclic Chem. 1995;32:1171-1175.
Rocca et al., Connection between metalation and cross-coupling strategies. A new convergent route to azacarbazoles. Tetrahedron. 1993;49(1):49-64.
Rollins, Chemokines. Blood. Aug. 1, 1997;90(3):909-28. Review.
Rosenberg et al., Treatment of 283 consecutive patients with metastatic melanoma or renal cell cancer using high-dose bolus interleukin 2. JAMA. Mar. 23-30, 1994;271(12):907-13.
Rothel et al., The use of recombinant ovine IL-1beta and TNF-alpha as natural adjuvants and their physiological effects in vivo. Immunol Cell Biol. Apr. 1998;76(2):167-72.
Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.
Royals et al., Studies in mixed ester condensations. IV. Acylations with methyl dimethoxyacetate. J Am Chem Soc. 1956;78:4161-4164.
Rozman et al., Chronic lymphocytic leukemia. N Engl J Med. Oct. 19, 1995;333(16):1052-7.
Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.
Salaun et al., TLR3 Can Directly Trigger Apoptosis in Human Cancer Cells. J of Immunology. 2006;176:4894-901.
Salemink, Uber 2-Propyl-1- Und 2-Propyl-Desaza-Adenin. Recueil. 1961;80:545-55. German.
Sambhi et al., Local production of tumor necrosis factor encoded by recombinant vaccinia virus is effective in controlling viral replication in vivo. Proc Natl Acad Sci U S A. May 1, 1991;88(9):4025-9.
Sams et al.; Necrotic arachnidism. J Am Acad Dermatol. Apr. 2001;44(4):561-73; quiz 573-6.
Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.
Scheerlinck, Genetic adjuvants for DNA vaccines. Vaccine. Mar. 21, 2001;19(17-19):2647-56.
Scheuer et al., Application of the Ritter reaction to mesityl oxide and chalcone. J Am Chem Soc. 1957;22:674-676.
Schofield et al., Reply. Low-Dose Interferon-alpha in Chronic Myeloid Leukemia. Ann Internal Med. 1995;122(9):728-29. 1 page.
Schwandner et al., Peptidoglycan- and lipoteichoic acid-induced cell activation is mediated by toll-like receptor 2. J Biol Chem. Jun. 18, 1999;274(25):17406-9.
Seeman et al., Steric and Conformational Effects in Nicotine Chemistry. J Org Chem. 1981;46:3040-48.

(56) References Cited

OTHER PUBLICATIONS

Serrat et al., A highly efficient and straightforward stereoselective synthesis of novel chiral α-acetylenic ketones. Tetrahedron: Assymmetry. 1999;10:3417-30.
Severa et al., Sensitization to TLR7 agonist in IFN-beta-preactivated dendritic cells. J Immunol. May 15, 2007;178(10):6208-16.
Seymour et al., Cellular immunity and hypersensitivity as components of periodontal destruction. Oral Dis. Mar. 1996;2(1):96-101. Review.
Shelburne et al., Quantitation of Bacteroids forsythus in subgingival plaque comparison on immunoassay and quantitative polymerase chain reaction. J Microbiol Methods. 2000;39:97-107.
Sidky et al., Inhibition of murine tumor growth by an interferon-inducing imidazoquinolinamine. Cancer Res. Jul. 1, 1992;52(13):3528-33.
Siegal et al., The nature of the principal type 1 interferon-producing cells in human blood. Science. Jun. 11, 1999;284(5421):1835-7.
Sletzinger et al., The Synthesis of Isomethadone. J Am Chem Soc. 1952;74:5619-20.
Smith et al., The role of polymorphonuclear leukocytes in the lesion caused by the venom of the brown spider, Loxosceles reclusa. Lab Invest. Jan. 1970;22(1):90-3.
Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.
Sommer et al., Recent Findings on How Proinflammatory Cytokines Cause Pain: Peripheral Mechanisms in Inflammatory and Neuropathic Hyperalgesia. Neurosci Letts. 2004;361:184-87.
Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.
Soria et al., Effect of food on the pharmacokinetics and bioavailability of oral imiquimod relative to a subcutaneous dose. Int J Clin Pharmacol Ther. Oct. 2000;38(10):476-81.
Spaner et al., A phase I/II trial of TLR-7 agonist immunotherapy in chronic lymphocytic leukemia. Leukemia. 2010; 24:222-26.
Spaner et al., Immunomodulatory effects of Toll-like receptor-7 activation on chronic lymphocytic leukemia cells. Leukemia. Feb. 2006;20(2):286-95.
Spaner et al., Toll-like receptor agonists in the treatment of chronic lymphocytic leukemia. Leukemia. Jan. 2007;21(1):53-60. Epub Oct. 26, 2006.
Spivey et al., Configurationally stable biaryl analogues of 4-(dimethylamino)pyridine: A novel class of chiral nucleophilic catalysts. J Org Chem. 1999;64:9430-9443.
Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.
Stack, Images in clinical medicine. Latrodectus mactans. N Engl J Med. Jun. 5, 1997;336(23):1649.
Stanley, Imiquimod and the imidazoquinolones: mechanism of action and therapeutic potential. Clin Exp Dermatol. Oct. 2002;27(7):571-7. Review.
Stashenko et al., Periapical inflammatory responses and their modulation. Crit Rev Oral Biol Med. 1998;9(4):498-521.
Steele et al., Lipoxygenase inhibitors as potential cancer chemopreventives. Cancer Epidemiol Biomarkers Prev. May 1999;8(5):467-83.
Steele of al., Potential use of lipoxygenase inhibitors for cancer chemoprevention. Expert Opin Investig Drugs. Sep. 2000;9(9):2121-38.
Steinmann et al., Topical imiquimod treatment of a cutaneous melanoma metastasis. J Am Acad Dermatol. Sep. 2000;43(3):555-6.
Stewart of al., Synthesis of a Carba-analog of S-Acetyl Coenzyme A,Acetonyl-dethio Coenzyme A; an Effective Inhibitor of Citrate Synthase. Liebigs Ann Chem. 1978:57-65.
Stillings et al., Substituted 1,3,4-thiadiazoles with anticonvulsant activity. 2. Aminoalkyl derivatives. J Med Chem. Nov. 1986;29(11):2280-4.
Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.
Stringfellow, Induction of interferon with low molecular weight compounds: fluorenone esters, ethers (tilorone), and pyrimidinones. Methods Enzymol. 1981;78(Pt A):262-84.
Ströher et al., Progress towards the treatment of Ebola haemorrhagic fever. Expert Opin Investig Drugs. Dec. 2006;15(12):1523-35.
Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475:Abstract 3030.
Surrey et al., The Synthesis of Some 3-Nitro- and 3-Amino-4-dialkylaminoalkylaminoquinoline Derivatives. J Am Chem Soc. 1951;73:2413-16.
Takeichi of al., Cytokine profiles of T-lymphocytes from gingival tissues with pathological pocketing. J Dent Res. Aug. 2000;79(8):1548-55.
Takeshita et al., Signal transduction pathways mediated by the interaction of CpG DNA with Toll-like receptor 9. Semin Immunol. Feb. 2004;16(1):17-22.
Takeuchi et al., Discrimination of bacterial lipoproteins by Toll-like receptor 6. Int Immunol. Jul. 2001;13(7):933-40.
Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.
Thesing et al., [Darstellung und Eigenschaften des $\Delta^1$-Pyrrolin-$N$-oxyds.]. Chem Ber. 1959;92:1748-55. German.
Thiruvikraman et al., Synthesis and reactions of pyrazolo-[3,4-c]quinoline derivatives. Indian Journal of Chemistry. 1987;26B:695-696.
Tomai et al., Imiquimod: in vivo and in vitro characteristics and toxicology. In: Cutaneous Infection and Therapy. Aly et al., eds. Marcel Dekkar, Inc., New York. 1997:405-15.
Tomic et al., Sensitization of IL-2 Signaling through TLR-7 Enhances B Lymphoma Cell Immunogenicity. J Immunol. 2006;176:3830-39.
Tomioka et al., Asymmetric Alkylation of α-Alkyl β-Keto Esters. J Am Chem Soc. 1984;106:2718-19.
Totterman et al., Phorbol ester-induced differentiation of chronic lymphocytic leukaemia cells. Nature. Nov. 13, 1980;288(5787):176-8.
Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.
Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.
Urosevic et al., Imiquimod treatment induces expression of opioid growth factor receptor: a novel tumor antigen induced by interferon-alpha? Clin Cancer Res. Aug. 1, 2004;10(15):4959-70.
Van De Kerhof, New Immunomodulatory Drugs. In: Skin and Environment: Perception and Protection. Ring et al., eds., 10th EADV Congress, Oct. 10-14, Munich, Germany. 2001:1:343-48.
Vasilakos et al., Adjuvant Activities of Immune Response Modifier R-848: Comparison with CoG ODN. Cell Immunol. 2000;204:64-74.
Vieweg et al., Tumor vaccines: from gene therapy to dendritic cells-the emerging frontier. Urol Clin North Am. Aug. 2003;30(3):633-43.
Vilcek, The cytokines: An overview. In: The Cytokine Handbook, Fourth Ed. M. Lotze and A.W. Thompson (eds.), 2003;1:3-14.
Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nucleic Acid Drug Dev. Jun. 2002;12(3):165-75.

(56) References Cited

OTHER PUBLICATIONS

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wexler et al., Accurate identification of experimental pulmonary metastases. J Natl Cancer Inst. Apr. 1966;36(4):641-5.

Wibaut et at., Syntheses of 3,4-Dimethylpyridine, 2,3-Dimethylpridine and 2-Methyl-3-Ethylpyridine. Rec Trav Chim. 1944;63:231-38.

Wierda et al, CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

\* cited by examiner

ARYLALKENYL AND ARYLALKYNYL SUBSTITUTED IMIDAZOQUINOLINES

RELATED APPLICATIONS

This application is the National Stage of International Application No. PCT/US2004/042556, filed Dec. 17, 2004, which claims priority to U.S. Provisional Application Ser. No. 60/532,982, filed Dec. 29, 2003, which is incorporated herein by reference.

FIELD OF THE INVENTION

This invention relates to derivatives of imidazoquinoline compounds and to pharmaceutical compositions containing the compounds. A further aspect of this invention relates to the use of these compounds as immunomodulators, for inducing cytokine biosynthesis in animals and in the treatment of diseases including viral and neoplastic diseases.

BACKGROUND OF THE INVENTION

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

There continues to be interest in and a need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula (I):

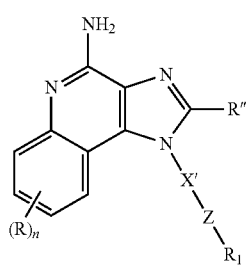

(I)

and more specifically of the following Formula (II):

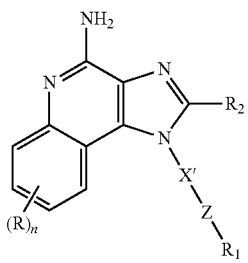

(II)

wherein: R, n, R", $R_1$, $R_2$, X', and Z are as defined below.

The compounds of Formulas I and II are useful as immune response modifiers (IRMs) due to their ability to induce cytokine biosynthesis (e.g., induce the biosynthesis or production of one or more cytokines) and otherwise modulate the immune response when administered to animals. The compounds are useful in the treatment of a variety of conditions such as viral diseases, and neoplastic diseases that are responsive to such changes in the immune response.

In another aspect, the present invention provides pharmaceutical compositions containing the immune response modifier compounds, and methods of inducing cytokine biosynthesis in an animal, treating a viral disease in an animal, and treating a neoplastic disease in an animal, by administering an effective amount of one or more compounds of Formula I (and more specifically, of Formula II) and/or pharmaceutically acceptable salts thereof to the animal.

In another aspect, the invention provides methods of synthesizing compounds of Formulas I and II and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides a new class of compounds that are useful in inducing cytokine biosynthesis in animals. Such compounds are of the following Formula (I):

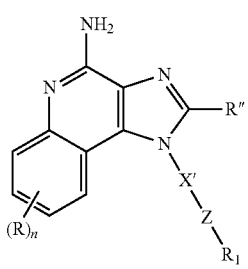

(I)

and more specifically of the following Formula (II):

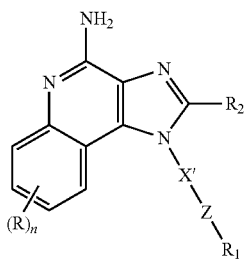

as well as intermediates for the preparation of compounds of Formulas (I) and (II), wherein the intermediates are of the following Formulas (III) and (IV):

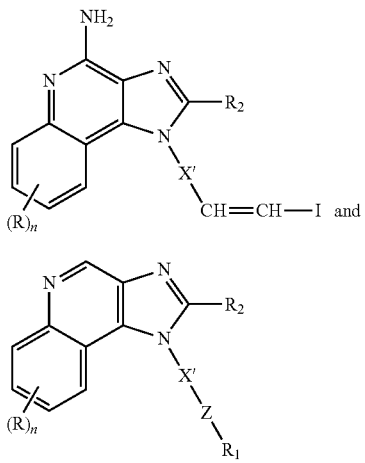

wherein: R, n, R", $R_1$, $R_2$, X', and Z are as defined below.

In one embodiment, the present invention provides compounds of the following Formula (I):

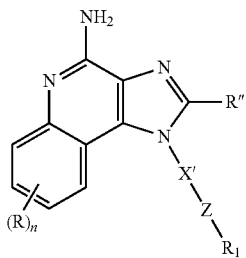

wherein:
Z is —CH═CH— or —C≡C—;
X' is —CH($R_3$)—, —CH($R_3$)-alkylene-, or —CH($R_3$)-alkenylene-;
$R_1$ is selected from the group consisting of:
—Ar,
—Ar'—Y—$R_4$,
—Ar'—X—Y—$R_4$, and
—Ar'—$R_5$;
Ar is selected from the group consisting of aryl and heteroaryl both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar' is selected from the group consisting of arylene and heteroarylene both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and wherein the alkylene, alkenylene, and alkynylene groups can be optionally interrupted by one or more —O— groups;

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

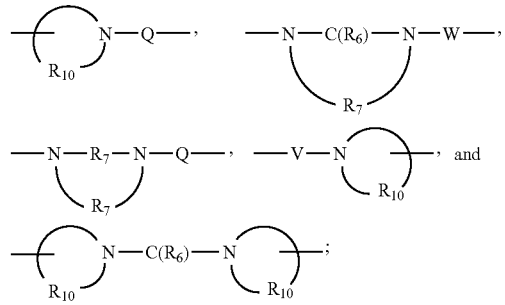

$R_3$ is hydrogen or $C_{1-10}$ alkyl;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of

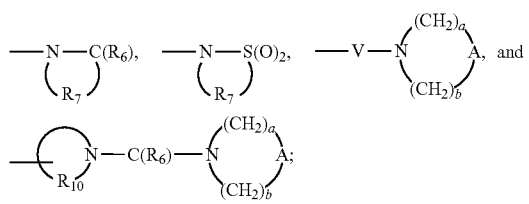

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
a and b are independently integers from 1 to 6 with the proviso that a+b is ≤7;
R is selected from the group consisting of alkyl, alkoxy, hydroxy, halogen, and trifluoromethyl; and
n is 0 or 1;
R" is hydrogen or a non-interfering substituent; or a pharmaceutically acceptable salt thereof.

In one embodiment, the present invention also provides compounds of the following Formula II:

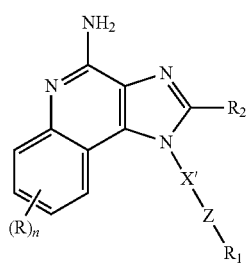

(II)

wherein:
Z is —CH=CH— or —C≡C—;
X' is —CH(R$_3$)—, —CH(R$_3$)-alkylene-, or —CH(R$_3$)-alkenylene-;
$R_1$ is selected from the group consisting of:
—Ar,
—Ar'—Y—R$_4$,
—Ar'—X—Y—R$_4$, and
—Ar'—R$_5$;

Ar is selected from the group consisting of aryl and heteroaryl both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar' is selected from the group consisting of arylene and heteroarylene both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

$R_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and wherein the alkylene, alkenylene, and alkynylene groups can be optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
O—C(R$_6$)—N(R$_8$)—,
—C(R$_6$)—N(OR$_9$)—,

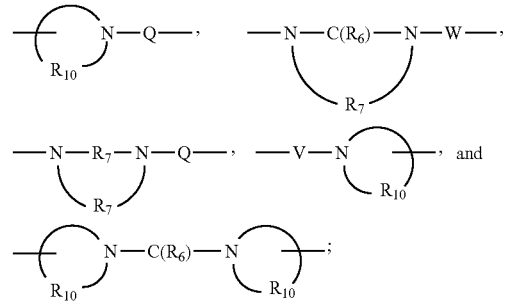

$R_3$ is hydrogen or $C_{1-10}$ alkyl;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

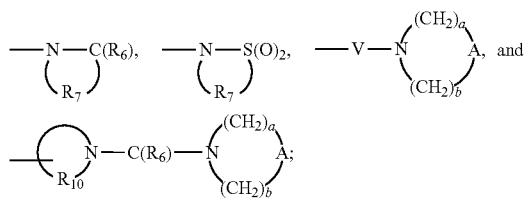

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$— and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
a and b are independently integers from 1 to 6 with the proviso that a+b is ≤7;
R is selected from the group consisting of alkyl, alkoxy, hydroxy, halogen, and trifluoromethyl; and
n is 0 or 1;
or a pharmaceutically acceptable salt thereof.

In another aspect, the present invention provides compounds, which are useful, for example, in preparing compounds of Formulas I and II.

In one embodiment, the present invention provides compounds of Formula III:

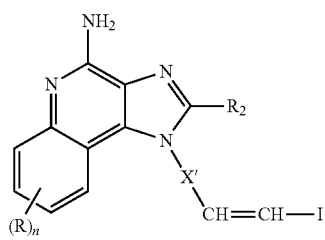

(III)

wherein:
X' is —CH(R$_3$)—, —CH(R$_3$)-alkylene-, or —CH(R$_3$)-alkenylene-;
$R_2$ is selected from the group consisting of:
—R$_4$,
—X—R$_4$,
—X—Y—R$_4$, and
—X—R$_5$;
X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and wherein the alkylene, alkenylene, and alkynylene groups can be optionally interrupted by one or more —O— groups;
Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
O—C(R$_6$)—N(R$_8$)—,
—C(R$_6$)—N(OR$_9$)—,

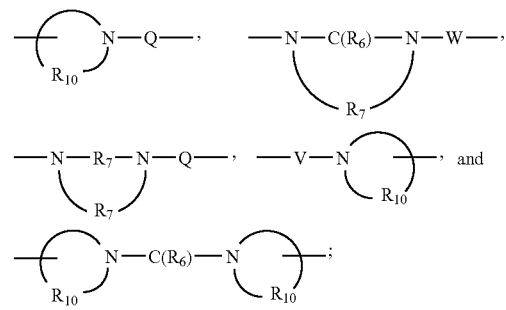

$R_3$ is hydrogen or $C_{1-10}$ alkyl;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of

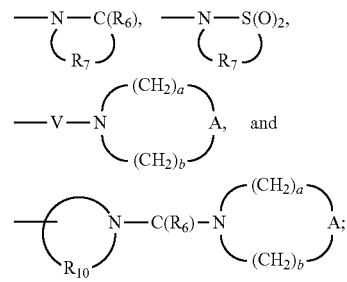

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

R is selected from the group consisting of alkyl, alkoxy, hydroxy, halogen, and trifluoromethyl; and n is 0 or 1;

or a pharmaceutically acceptable salt thereof.

In another embodiment, the present invention provides compounds of the Formula IV:

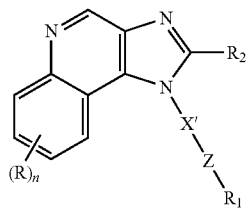

(IV)

wherein:

Z is —CH=CH— or —C≡C—;

X' is —CH(R$_3$)—, —CH(R$_3$)-alkylene-, or —CH(R$_3$)-alkenylene-;

R$_1$ is selected from the group consisting of:
—Ar,
—Ar'—Y—R$_4$,
—Ar'—X—Y—R$_4$, and
—Ar'—R$_5$;

Ar is selected from the group consisting of aryl and heteroaryl both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

Ar' is selected from the group consisting of arylene and heteroarylene both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

R$_2$ is selected from the group consisting of:
—R$_4$,
—X—R$_4$,
—X—Y—R$_4$, and
—X—R$_5$;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and wherein the alkylene, alkenylene, and alkynylene groups can be optionally interrupted by one or more —O— groups;

Y is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,

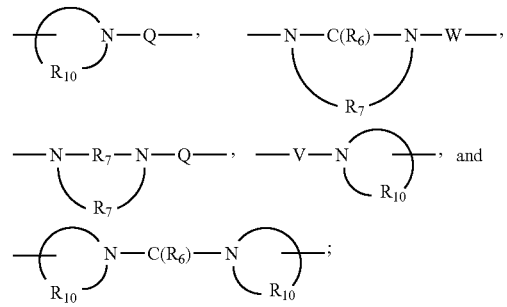

R$_3$ is hydrogen or C$_{1-10}$ alkyl;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of

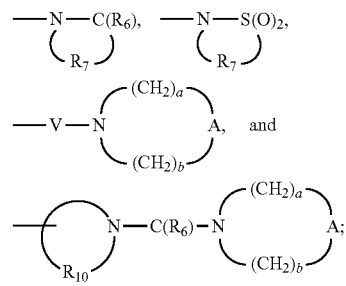

R$_6$ is selected from the group consisting of =O and =S;

R$_7$ is C$_{2-7}$ alkylene;

R$_8$ is selected from the group consisting of hydrogen, alkyl, alkoxyalkylenyl, and arylalkylenyl;

R$_9$ is selected from the group consisting of hydrogen and alkyl;

R$_{10}$ is C$_{3-8}$ alkylene;

A is selected from the group consisting of —O—, —C(O)—, —S(O)$_{0-2}$—, —CH$_2$—, and —N(R$_4$)—;

Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;

V is selected from the group consisting of —C($R_6$)—, —O—C($R_6$)—, —N($R_8$)—C($R_6$)—, and —S(O)$_2$—;

W is selected from the group consisting of a bond, —C(O)—, and —S(O)$_2$—;

a and b are independently integers from 1 to 6 with the proviso that a+b is ≤7;

R is selected from the group consisting of alkyl, alkoxy, hydroxy, halogen, and trifluoromethyl; and n is 0 or 1;

or a pharmaceutically acceptable salt thereof.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are used when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

Herein, "non-interfering" means that the ability of the compound or salt, which includes a non-interfering substituent, to modulate the biosynthesis of one or more cytokines is not destroyed by the non-interfering substituent. For certain embodiments, R" is hydrogen or a non-interfering substituent. Illustrative non-interfering R" groups include those described above for $R_2$.

When a group (or substituent or variable) is present more than once in any Formula described herein, each group (or substituent or variable) is independently selected, whether explicitly stated or not. For example, when an $R_1$ and an $R_2$ group both contain an $R_4$ group, each $R_4$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., R, n, R", $R_1$, $R_2$, X', and Z, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, $R_1$ is selected from the group consisting of alkyl, alkoxy, hydroxy, halogen, and trifluoromethyl.

For certain embodiments, $R_1$ is selected from the group consisting of —Ar, —Ar'—Y—$R_4$, —Ar'—X—Y—$R_4$; and —Ar'—$R_5$. For certain embodiments, particularly embodiments of Formula II, $R_1$ is —Ar. In other embodiments, particularly embodiments of Formula II, $R_1$ is selected from the group consisting of 2-pyridinyl, 3-pyridinyl, and phenyl wherein the phenyl group can be unsubstituted or substituted by alkoxy, haloalkyl, halogen, nitro, or cyano. For certain embodiments, $R_1$ is phenyl, 3-chlorophenyl, 4-chlorophenyl, 3-fluorophenyl, 4-fluorophenyl, 3-methoxyphenyl, 4-methoxyphenyl, 3-trifluoromethylphenyl, 4-trifluoromethylphenyl, 2-pyridinyl, or 3-pyridinyl.

For certain embodiments, R" is hydrogen or a non-interfering substituent. Illustrative non-interfering R" groups include those described above for $R_2$.

For certain embodiments, $R_2$ is selected from the group consisting of —$R_4$, —X—$R_4$, —X—Y—$R_4$, and —X—$R_5$.

For certain embodiments, particularly embodiments of Formula II, $R_2$ is selected from the group consisting of hydrogen, alkyl, and alkoxyalkylenyl. For certain embodiments, particularly embodiments of Formula II, n is 0 and $R_2$ is selected from the group consisting of hydrogen, alkyl, and alkoxyalkylenyl. For certain embodiments, particularly embodiments of Formula II, $R_2$ is selected from the group consisting of methyl, ethyl, propyl, butyl, ethoxymethyl, and 2-methoxyethyl.

For certain embodiments, $R_3$ is hydrogen or $C_{1-10}$ alkyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_5$ is selected from the group consisting of

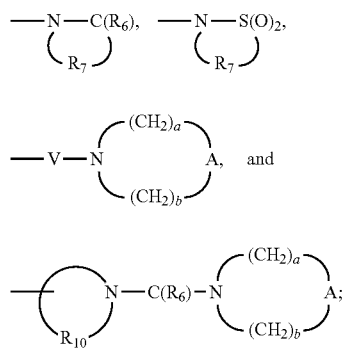

For certain embodiments, $R_6$ is selected from the group consisting of =O and =S.

For certain embodiments, $R_7$ is $C_{2-7}$ alkylene.

For certain embodiments, $R_8$ is selected from the group consisting of hydrogen, alkyl, alkoxyalkylenyl, and arylalkylenyl.

For certain embodiments, $R_9$ is selected from the group consisting of hydrogen and alkyl.

For certain embodiments, $R_{10}$ is $C_{3-8}$ alkylene.

For certain embodiments, A is selected from the group consisting of —O—, —C(O)—, —S(O)$_{0-2}$—, —CH$_2$—, and —N(R$_4$)—.

For certain embodiments, Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—.

For certain embodiments, V is selected from the group consisting of —C(R$_6$)—, —O—C(R$_6$)—, —N(R$_8$)—C(R$_6$)—, and —S(O)$_2$—.

For certain embodiments, W is selected from the group consisting of a bond, —C(O)—, and —S(O)$_2$—.

For certain embodiments, X' is —CH(R$_3$)—, —CH(R$_3$)-alkylene-, or —CH(R$_3$)-alkenylene-. For certain embodiments, particularly of Formula II, X' is selected from the group consisting of —CH$_2$—C(CH$_3$)$_2$—, methylene, and propylene. For certain embodiments, X' is selected from the group consisting of —CH$_2$—, —(CH$_2$)$_2$—, and —(CH$_2$)$_3$—.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and wherein the alkylene, alkenylene, and alkynylene groups can be optionally interrupted by one or more —O— groups.

For certain embodiments, Y is selected from the group consisting of —S(O)$_{0-2}$—, —S(O)$_2$—N(R$_8$)—, —C(R$_6$)—, —C(R$_6$)—O—, —O—C(R$_6$)—, —O—C(O)—O—, —N(R$_8$)-Q-, —C(R$_6$)—N(R$_8$)—, —O—C(R$_6$)—N(R$_8$)—, —C(R$_6$)—N(OR$_9$)—,

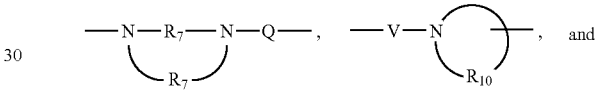

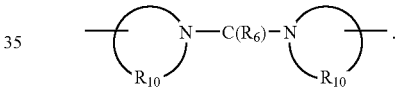

For certain embodiments, Z is —CH=CH— or —C≡C—. For some embodiments, particularly embodiments of Formula II, Z is —C≡C—. In other embodiments, particularly of Formula II, Z is —CH=CH—.

For certain embodiments, Ar is selected from the group consisting of aryl and heteroaryl both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino.

For certain embodiments, Ar' is selected from the group consisting of arylene and heteroarylene both of which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino.

For certain embodiments, a and b are independently integers from 1 to 6 with the proviso that a+b is ≤7.

For certain embodiments, n is 0 or 1. For certain embodiments, n is 0.

Preparation of the Compounds

Compounds of the invention can be prepared according to Reaction Scheme I, wherein R, $R_1$, $R_2$, X', and n are as defined above. In step (1) of Reaction Scheme I, an alkynyl amine of Formula HC≡C—X'—NH$_2$ is added to a 4-chloro-3-nitroquinoline of Formula V to afford an alkynyl-substituted 3-nitroquinolin-4-amine of Formula VI. The reaction is conveniently carried out by combining the alkynyl amine of Formula HC≡C—X'—NH$_2$ with a quinoline of Formula V in the presence of a base such as triethylamine in a suitable solvent such as dichloromethane or tetrahydrofuran. The reaction can be carried out at ambient temperature, and the product can be isolated using conventional methods. Some amines of Formula HC≡C—X'—NH$_2$, such as propargylamine, are commercially available; others can be prepared by known synthetic methods. Compounds of Formula V are known and can be prepared according to known methods. See, for example, U.S. Pat. Nos. 4,689,338; 4,929,624; 5,268,376; 5,346,905; 5,389,640; and 5,756,747.

In step (2) of Reaction Scheme I, an alkynyl-substituted 3-nitroquinolin-4-amine of Formula VI is reduced to an alkynyl-substituted quinoline-3,4-diamine of Formula VII. The reduction of the nitro group is conveniently carried out by adding an aqueous solution of sodium dithionite to an alkynyl-substituted 3-nitroquinolin-4-amine of Formula VI in a suitable solvent such as ethanol. The reaction can be carried out at ambient temperature, and the product can be isolated by conventional methods.

In step (3) of Reaction Scheme I, a quinoline-3,4-diamine of Formula VII is treated with a carboxylic acid equivalent to provide a 1H-imidazo[4,5-c]quinoline of Formula VIII. Suitable carboxylic acid equivalents include orthoesters of Formula R$_2$C(O-alkyl)$_3$, 1,1-dialkoxyalkyl alkanoates of Formula R$_2$C(O-alkyl)$_2$(O—C(O)-alkyl), and acid chlorides of Formula R$_2$C(O)Cl. The selection of the carboxylic acid equivalent is determined by the desired substituent at R$_2$. For example, triethyl orthopropionate will provide a compound where R$_2$ is ethyl, and trimethyl orthovalerate will provide a compound where R$_2$ is a butyl group. The reaction is conveniently carried out by adding the carboxylic acid equivalent to a quinoline-3,4-diamine of Formula VII in a suitable solvent such as toluene or pyridine. Optionally, catalytic pyridine hydrochloride can be added. The reaction is carried out at a temperature high enough to drive off alcohol or water formed during the reaction, for example, at the reflux temperature of the solvent.

Alternatively, step (3) can be carried out in two steps when an acid chloride of Formula R$_2$C(O)Cl is used as the carboxylic acid equivalent. Part (i) of step (3) is conveniently carried out by adding the acid chloride to a solution of a quinoline 3,4-diamine of Formula VII in a suitable solvent such as dichloromethane or acetonitrile to afford an amide. Optionally, a tertiary amine such as triethylamine, pyridine, or 4-dimethylaminopyridine can be added. The reaction can be carried out at ambient temperature or at an elevated temperature. The amide product can be isolated and optionally purified using conventional techniques. Part (ii) of step (3) involves heating the amide prepared in part (i) to provide a 1H-imidazo[4,5-c]quinoline of Formula VIII. The reaction is conveniently carried out in a suitable solvent such as toluene at a temperature sufficient to drive off water formed during the reaction. The reaction can also be carried out in a solvent such as ethanol or methanol in the presence of a base such as triethylamine. The product can be isolated using conventional methods.

In step (4a) of Reaction Scheme I, a 1H-imidazo[4,5-c] quinoline of Formula VIII is oxidized to provide a 1H-imidazo[4,5-c]quinoline-5N-oxide of Formula IX using a conventional oxidizing agent capable of forming N-oxides. The reaction is conveniently carried out by adding 3-chloroperoxybenzoic acid to a compound of Formula VIII in a solvent such as dichloromethane or chloroform. The reaction can be carried out at ambient temperature, and the product can be isolated using conventional methods.

In step (5a) of Reaction Scheme I, a 1H-imidazo[4,5-c] quinoline-5N-oxide of Formula IX is aminated to provide a 1H-imidazo[4,5-c]quinolin-4-amine of Formula X. Step (5a) can be carried out by the activation of an N-oxide of Formula IX by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula IX in a suitable solvent such as dichloromethane or chloroform and then adding p-toluenesulfonyl chloride. The reaction can be carried out at ambient temperature. The product or pharmaceutically acceptable salt thereof can be isolated using conventional methods.

Steps (4a) and (5a) may also be carried out as a one-pot procedure by first adding 3-chloroperoxybenzoic acid to a 1H-imidazo[4,5-c]quinoline of Formula VIII in a solvent such as dichloromethane or chloroform. After the reaction is stirred for a period long enough to complete the oxidation, ammonium hydroxide and p-toluenesulfonyl chloride are sequentially added. The reaction can be carried out at ambient temperature, and the product of Formula X can be isolated using conventional methods.

In step (6a) of Reaction Scheme I, an alkynyl-substituted 1H-imidazo[4,5-c]quinolin-4-amine of Formula X undergoes a Sonogashira coupling reaction with an aryl or heteroaryl iodide of Formula R$_1$—I to provide an arylalkynyl-substituted 1H-imidazo[4,5-c]quinolin-4-amine of Formula XI, a subgenus of Formula II. Numerous iodides of Formula R$_1$—I are commercially available; others can be prepared by known synthetic methods. The reaction is conveniently carried out by adding an iodide of Formula R$_1$—I to an alkynyl-substituted 1H-imidazo[4,5-c]quinolin-4-amine of Formula X in the presence of catalytic amounts of copper (I) iodide and tris(dibenzylideneacetone)dipalladium(0) chloroform adduct and a base such as triethylamine. The coupling reaction is carried out in a suitable solvent such as N,N-dimethylformamide (DMF) at ambient temperature. The product or pharmaceutically acceptable salt thereof can be isolated by conventional methods.

Steps (4a), (5a), and (6a) may also be carried out in a different order, as shown in steps (4b), (5b), and (6b) of Reaction Scheme I. In step (4b) of Reaction Scheme I, an alkynyl-substituted 1H-imidazo[4,5-c]quinoline of Formula VIII undergoes a Sonogashira coupling reaction with an aryl or heteroaryl iodide of Formula R$_1$—I to provide an arylalkynyl-substituted 1H-imidazo[4,5-c]quinoline of Formula XII, a subgenus of Formula IV. The reaction can be carried out as described in step (6a) above.

In steps (5b) and (6b) of Reaction Scheme I, an arylalkynyl-substituted 1H-imidazo[4,5-c]quinoline of Formula XII is first oxidized to an arylalkynyl-substituted 1H-imidazo[4,5-c]quinoline-5N-oxide of Formula XIII, which is then aminated to provide an arylalkynyl-substituted 1H-imidazo[4,5-c]quinolin-4-amine of Formula XI. Steps (5b) and (6b) can be carried out as described for steps (4a) and (5a) above. The product of Formula XI or a pharmaceutically acceptable salt thereof may be isolated using conventional methods.

Reaction Scheme I

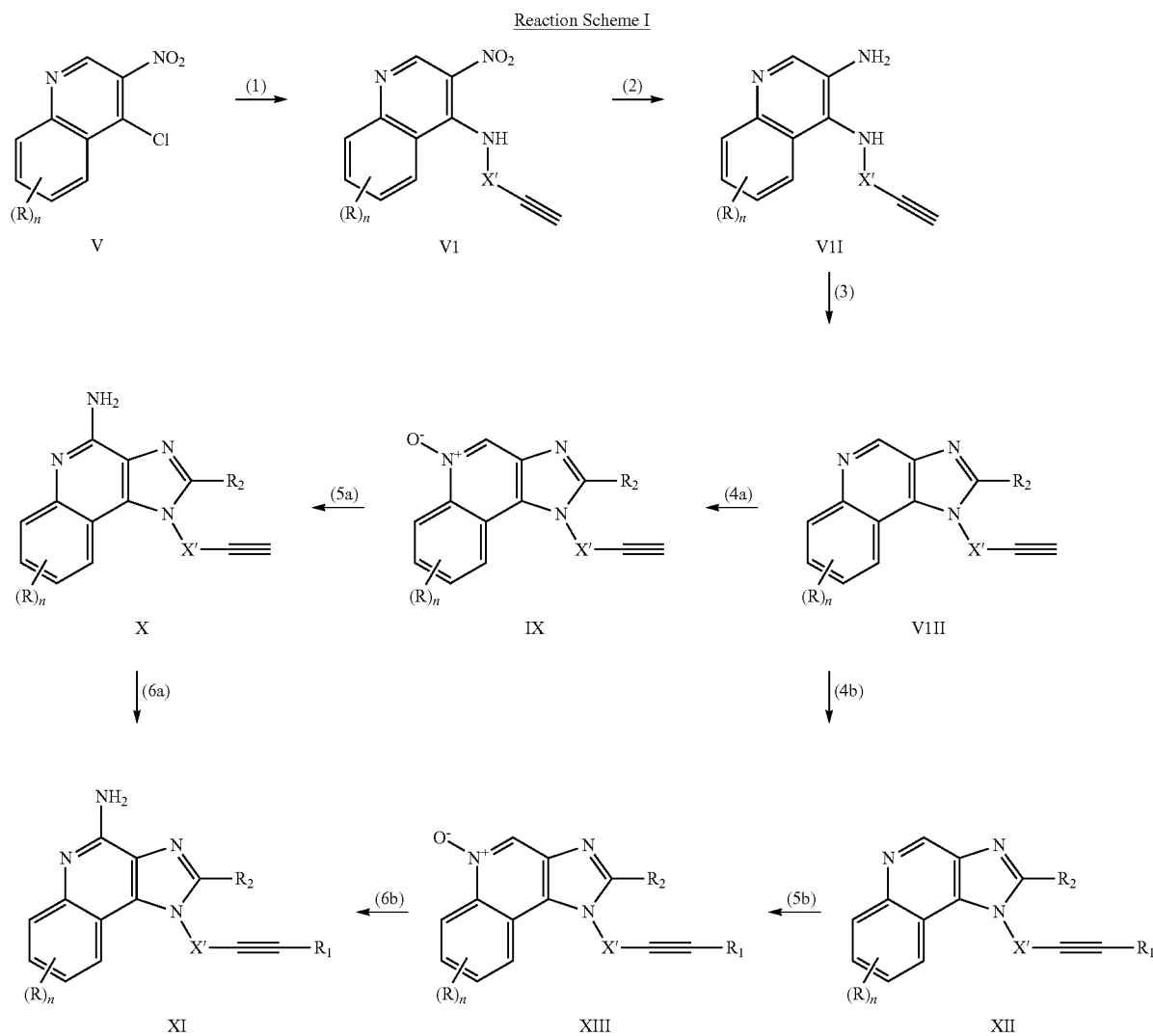

Compounds of the invention can also be prepared according to Reaction Scheme II, wherein R, $R_1$, $R_2$, X', and n are as defined above. In step (1) of Reaction Scheme II, a 1H-imidazo[4,5-c]quinolin-1-yl alcohol of Formula XIV is oxidized to provide an aldehyde-substituted 1H-imidazo[4,5-c]quinoline of Formula XV using conventional methods, for example, Swern oxidation conditions. Many compounds of Formula XIV are known; see for example, Gerster, U.S. Pat. No. 4,689,338. Others can be readily prepared using known synthetic routes; see for example, Gerster et al., U.S. Pat. No. 5,605,899 and Gerster, U.S. Pat. No. 5,175,296. The Swern oxidation is conveniently carried out by adding a compound of Formula XIV followed by triethylamine to a mixture of oxalyl chloride and dimethylsulfoxide in a suitable solvent, such as dichloromethane. The reaction can be carried out at sub-ambient temperatures, such as −78° C., and the product can be isolated using conventional methods.

In step (2) of Reaction Scheme II, an aldehyde-substituted 1H-imidazo[4,5-c]quinoline of Formula XV is converted to an alkynyl-substituted 1H-imidazo[4,5-c]quinoline of Formula VIII. The reaction is conveniently carried out by adding diethyl 1-diazo-2-oxopropylphosphonate to the aldehyde-substituted 1H-imidazo[4,5-c]quinoline of Formula XV in the presence of a mild base such as potassium carbonate. The reaction is carried out in a suitable solvent such as dichloromethane at ambient temperature. The product can be isolated using conventional methods.

In steps (3) and (4) of Reaction Scheme II, an alkynyl-substituted 1H-imidazo[4,5-c]quinoline of Formula VIII is first oxidized to an alkynyl-substituted 1H-imidazo[4,5-c]quinoline-5N-oxide of Formula IX, which is then aminated to provide an alkynyl-substituted 1H-imidazo[4,5-c]quinolin-4-amine of Formula X. Steps (3) and (4) are identical to steps (4a) and (5a) in Reaction Scheme I.

In step (5) of Reaction Scheme II an alkynyl-substituted 1H-imidazo[4,5-c]quinolin-4-amine of Formula X is coupled with an aryl or heteroaryl iodide of Formula $R_1$—I to provide an arylalkynyl-substituted 1H-imidazo[4,5-c]quinolin-4-amine of Formula XI, a subgenus of Formula II. Step (5) is identical to step (6a) in Reaction Scheme I. The product or pharmaceutically acceptable salt thereof can be isolated by conventional methods.

Reaction Scheme II

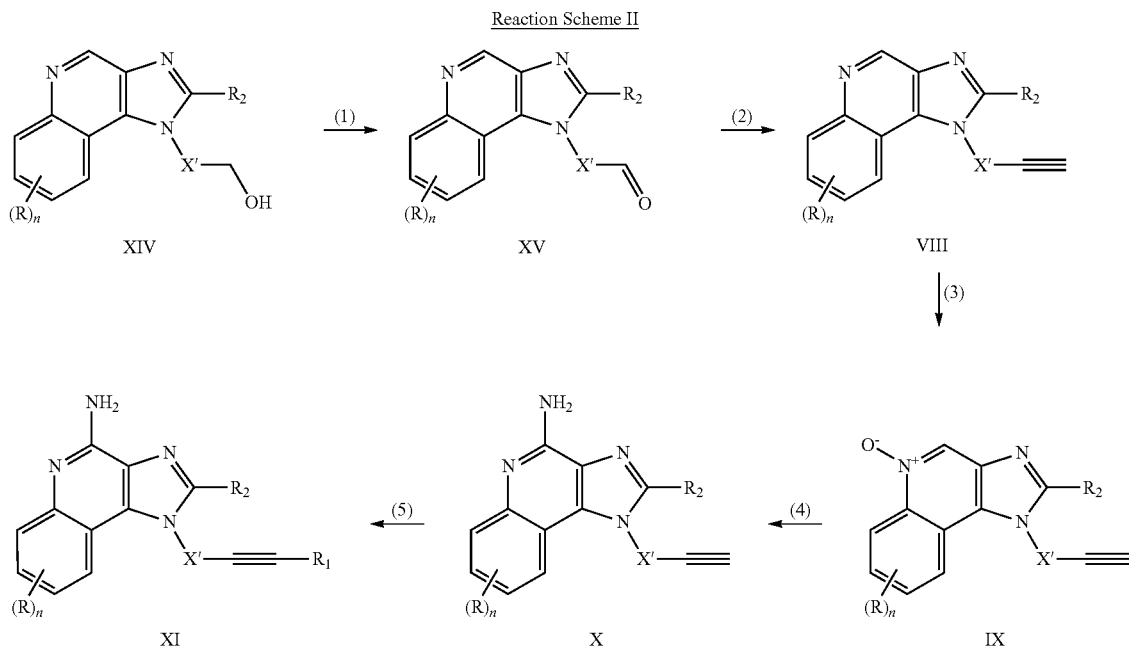

Arylalkenyl-substituted 1H-imidazo[4,5-c]quinolin-4-amines of the invention can be prepared according to Reaction Scheme m, wherein R, $R_1$, $R_2$, X', and n are as defined above. In step (1) of Reaction Scheme III, an alkynyl-substituted 1H-imidazo[4,5-c]quinoline of Formula VIII, prepared as described in Reaction Scheme I or Reaction Scheme II, is converted to a vinyl iodide of Formula XVI. The reaction can be carried out by hydrozirconation of the alkyne of Formula VIII and reaction of the resulting complex with iodine. The reaction is conveniently carried out by adding bis(cyclopentadienyl)zirconium chloride hydride (Schwartz's Reagent) to a solution of an alkynyl-substituted 1H-imidazo[4,5-c]quinoline of Formula VIII in a suitable solvent such as dichloromethane. The reaction can be carried out at a sub-ambient temperature such as 0° C. Solid iodine is then added to the intermediate complex to provide the vinyl iodide of Formula XVI. The product can be isolated by conventional methods.

In steps (2) and (3) of Reaction Scheme III, an alkenyl-substituted 1H-imidazo[4,5-c]quinoline of Formula XVI is first oxidized to an alkenyl-substituted 1H-imidazo[4,5-c]quinoline-5N-oxide of Formula XVII, which is then aminated to provide an alkenyl-substituted 1H-imidazo[4,5-c]quinolin-4-amine of Formula III. Steps (2) and (3) of Reaction Scheme III can be carried out as described in steps (4a) and (5a) in Reaction Scheme I.

In step (4) of Reaction Scheme III, the vinyl iodide of Formula III is coupled with a boronic acid of Formula $R_1$—B(OH)$_2$, an anhydride thereof, or a boronic acid ester of Formula $R_1$—B(O-alkyl)$_2$ to provide an arylalkenyl-substituted 1H-imidazo[4,5-c]quinolin-4-amine of Formula XVIII, which is a subgenus of Formula II. The Suzuki coupling is carried out by combining a compound of Formula III with a boronic acid or an ester or anhydride thereof in the presence of palladium (II) acetate, triphenylphosphine, and a base such as sodium carbonate in a suitable solvent mixture such as water and ethanol. The reaction can be carried out at an elevated temperature (e.g., 70° C.). Many boronic acids of Formula $R_1$—B(OH)$_2$, anhydrides thereof, and boronic acid esters of Formula $R_1$—B(O-alkyl)$_2$ are commercially available; others can be readily prepared using known synthetic methods. See, for example, Li, W. et al, *J. Org. Chem.*, 67, 5394-5397 (2002). The product or pharmaceutically acceptable salt thereof can be isolated using conventional methods.

Reaction Scheme III

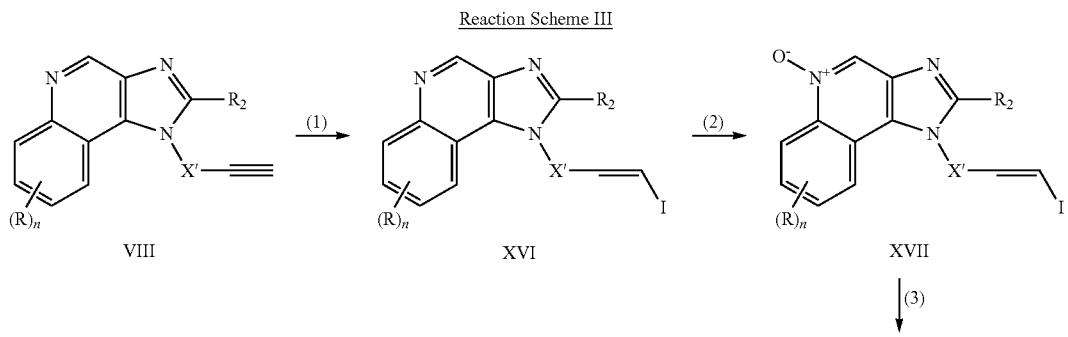

-continued

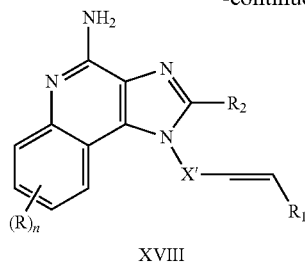

XVIII (4)

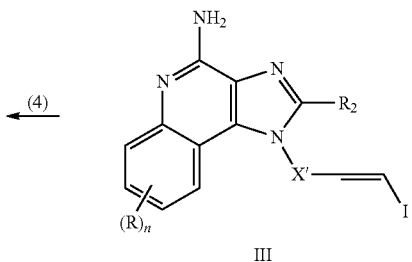

III

Compounds of the invention can also be prepared using variations of the synthetic routes shown in Reaction Schemes I through III. For example, in Reaction Scheme III in those instances where $R_1$ is not susceptible to oxidation, the Suzuki coupling can be carried out prior to the oxidation and amination. Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella*;

(c) other infectious diseases, such chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, compounds or salts of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

Objects and advantages of this invention are further illustrated by the following examples, but the particular materials and amounts thereof recited in these examples, as well as other conditions and details, should not be construed to unduly limit this invention.

EXAMPLES

Example 1

2-Ethyl-1-[3-(pyridin-3-yl)-2-propynyl]-1H-imidazo[4,5-c]quinolin-4-amine

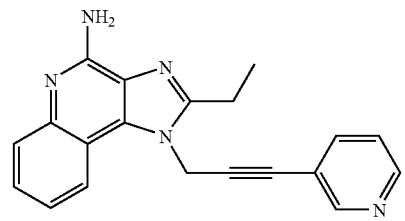 [SMILES: CCc1nc2c(N)nc3ccccc3c2n1CC#Cc1cccnc1]

Part A

Triethylamine (8.0 mL, 1.2 eq.) was added to a mixture of 4-chloro-3-nitroquinoline (10.0 g, 47.9 mmol, 1.0 eq.) in tetrahydrofuran (THF, 200 mL). Propargylamine (3.4 mL, 1.1 eq.) was added and the reaction mixture was stirred vigorously for 1.5 hours. The reaction mixture was concentrated under reduced pressure and the residue was partitioned between chloroform (700 mL) and water (200 mL). The organic layer was washed with water (1×200 mL). The combined aqueous layers were back extracted with chloroform (2×150 mL). The combined organics were dried over magnesium sulfate and concentrated under reduced pressure to provide 10.59 g of 4-chloro-3-nitro-N-(2-propynyl)quinoline as a yellow solid.

Part B

A solution of sodium dithionite (40.57 g of 85%, 5.0 eq.) in water (150 mL) was added over a period of 5 minutes to a vigorously stirred suspension of the material from Part A (10.59 g, 46.60 mmol, 1.0 eq.) in ethanol (460 mL). The reaction mixture was stirred for 20 minutes and then concentrated under reduced pressure. The residue was partitioned between chloroform (300 mL) and water (300 mL); the organic layer was separated. The aqueous layer was back extracted with additional chloroform. The combined organics were dried over magnesium sulfate and concentrated under reduced pressure to provide 3.06 g of $N^4$-(2-propynyl)quinoline-3,4-diamine as a pale yellow solid (lot 1). A small amount of methanol was added to the aqueous layer in the separatory funnel to dissolve an oily yellow material coating the separatory funnel. The aqueous layer was extracted with chloroform (5×150 mL). The combined extracts were dried over magnesium sulfate and concentrated under reduced pressure to provide 3.66 g of $N^4$-(2-propynyl)quinoline-3,4-diamine as a yellow solid (lot 2). Analysis by NMR showed ~80% purity. The aqueous layer was made basic (pH ~8) with aqueous saturated sodium bicarbonate and then extracted with chloroform (2×150 mL). The combined extracts were dried over magnesium sulfate and concentrated under reduced pressure to provide $N^4$-(2-propynyl)quinoline-3,4-diamine as a yellow oil, this material was combined with lot 2 for a total of 7.03 g.

Part C

A suspension of lot 1 (3.06 g, 15.5 mmol., 1.0 eq.) from Part B in a mixture of chloroform (15 mL) and toluene (135 mL) was warmed until most of the solid had gone into solution. Triethyl orthopropionate (3.4 mL, 1.1 eq) and pyridine hydrochloride (180 mg, 0.1 eq.) were added and the reaction mixture was heated at 110° C. for 1.5 hours. The reaction mixture was allowed to cool to ambient temperature and then concentrated under reduced pressure to provide crude product. The material from Part B lot 2 was cyclized using the same method. The combined crude products were purified by column chromatography (silica gel eluting with 10/90 methanol/chloroform) to provide 6.79 g of 2-ethyl-1-(2-propynyl)-1H-imidazo[4,5-c]quinoline as a light tan solid.

Part D

3-Chloroperoxybenzoic acid (1.21 g of 77%, 1.15 eq.) was added in a single portion to a solution of 2-ethyl-1-(2-propynyl)-1H-imidazo[4,5-c]quinoline (1.00 g, 4.25 mmol, 1.0 eq) in chloroform (42 mL). The reaction mixture was stirred at ambient temperature for 1 hour at which time analysis by thin layer chromatography (TLC) indicated that the reaction was complete. The reaction mixture was diluted with chloroform (150 mL) and washed with aqueous saturated sodium bicarbonate (2×50 mL). The combined aqueous layers were back extracted with chloroform (3×30 mL). The combined organics were dried over magnesium sulfate and concentrated under reduced pressure to provide 1.19 g of 2-ethyl-1-(2-propynyl)-1H-imidazo[4,5-c]quinoline 5-oxide as a white solid.

Part E

Ammonium hydroxide (43 mL) was added to a stirred suspension of the material from Part D in chloroform (43 mL). Tosyl chloride (0.89 g, 1.1 eq) was added and the reaction mixture was stirred vigorously for 2 hours. The reaction mixture was diluted with chloroform (30 mL) and the layers were separated. The aqueous layer was back extracted with chloroform (2×20 mL). The combined organics were dried over magnesium sulfate and concentrated under reduced pressure to provide a brown solid. This material was triturated with ethyl acetate (~20 mL), isolated by filtration, rinsed with ethyl acetate (3×7 mL) and dried under vacuum at 70° C. to provide 884 mg of an off white solid. This material was triturated with warm diethyl ether (15 mL), isolated by filtration, rinsed with diethyl ether (2×10 mL) to provide 857 mg of product. This material was recrystallized twice from dichloroethane (~40 mL) and dried under vacuum at 80° C. to provide 512 mg of 2-ethyl-1-(2-propynyl)-1H-imidazo[4,5-c]quinoline-4-amine as off-white crystals, mp 182-184° C. $^1$H NMR (300 MHz, DMSO-$d_6$) δ 8.20 (dd, J=1.0, 8.2 Hz, 1H), 7.61 (dd, J=1.0, 8.3 Hz, 1H), 7.43 (ddd, J=1.3, 7.0, 8.3 Hz, 1H), 7.26 (ddd, J=1.3, 7.0, 8.2 Hz, 1H), 6.49 (s, 2H), 5.42 (d, J=2.4 Hz, 2H), 3.51 (t, J=2.4 Hz, 1H), 2.99 (q, J=7.5 Hz, 2H), 1.37 (t, J=7.5 Hz, 3H); MS (APCI m/z 251 (M+H)$^+$; Anal. calcd for $C_{15}H_{14}N_4 \cdot 0.01C_2H_4Cl_2 \cdot 0.03H_2O$: C, 71.64; H, 5.64; N, 22.25. Found: C, 71.28; H, 5.63; N, 22.41. Karl Fischer (KF): 0.20.

Part F

Tris(dibenzylideneacetone)dipalladium(0) chloroform adduct (54.6 mg, 0.03 eq.), 3-iodopyridine (425 mg, 1.1 eq.), triethylamine (735 μL, 3.0 eq.), and copper (I) iodide (20.1 mg, 0.06 eq.) were added sequentially to a solution of 2-ethyl-1-(2-propynyl)-1H-imidazo[4,5-c]quinolin-4-amine (440 mg, 1.76 mmol, 1.0 eq.) in N,N-dimethylformamide (DMF, 18 mL). The reaction mixture was stirred at ambient temperature for 1 hour at which time analysis by 1H NMR showed that the reaction was complete. The reaction mixture was concentrated under reduced pressure and the residue purified by column chromatography (20 g of silica gel eluting with 10/90 methanol/chloroform) to provide 0.8 g of a light yellow solid. This material was triturated with water (~20 mL), isolated by filtration, rinsed with water (2×5 mL) and dried to give 0.50 g of tan solid. The solid was suspended in water (~10 mL), then made basic (pH ~11) with 10% aqueous sodium hydroxide, isolated by filtration, rinsed with water, and then triturated with methanol. The resulting material was dissolved in warm 10/90 methanol/chloroform (40 mL), absorbed onto silica gel (2 g) and eluted with 10/90 methanol/chloroform. The eluant was allowed to dry at ambient temperature overnight and then the residue was dried under vacuum at 80° C. overnight to provide 260 mg of 2-ethyl-1-[3-(pyridin-3-yl)-2-propynyl]-1H-imidazo[4,5-c]quinolin-4-amine hydroiodide as an off white powder, mp 249-251° C. (dec.). $^1$H NMR (300 MHz, DMSO-$d_6$) δ 13.24 (br s, 1H), 8.74 (br s, 2H), 8.54 (m, 3H), 7.86 (d, J=7.6 Hz, 1H), 7.78 (m, 2H), 7.65 (ddd, J=1.0, 8.2, 8.2 Hz, 1H), 7.39 (ddd, J=0.6, 4.9, 7.9 Hz, 1H), 5.86 (s, 2H), 3.14 (q, J=7.5 Hz, 2H), 1.44 (t, J=7.5 Hz, 3H); MS (APCI) m/z 328 (M+H)$^+$; Anal. calcd for $C_{20}H_{17}N_5 \cdot HI \cdot 0.02CHCl_3$: C, 52.54; H, 3.97; N, 15.30. Found: C, 52.68; H, 3.92; N, 15.25.

Example 2

2-Ethyl-1-[3-(thien-2-yl)-2-propynyl]-1H-imidazo[4,5-c]quinolin-4-amine

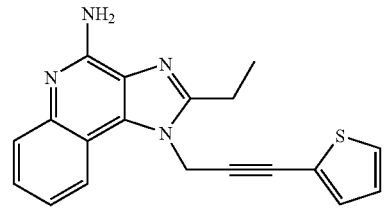 [SMILES: CCc1nc2c(N)nc3ccccc3c2n1CC#Cc1cccs1]

Tris(dibenzylideneacetone)dipalladium(0) chloroform adduct (62.1 mg, 0.03 eq.), 2-iodothiophene (0.46 g, 1.1 eq.), triethylamine (0.61 g, 3 eq.), and copper (I) iodide (23 mg, 0.06) were added sequentially to a solution of 2-ethyl-1-(2-propynyl)-1H-imidazo[4,5-c]quinolin-4-amine (0.5 g, 2.0 mmol, 1.0 eq) in DMF. The reaction mixture was stirred at ambient temperature for 3.5 hours. The reaction mixture was concentrated under reduced pressure to provide crude product which was purified by column chromatography (silica gel eluting with 5/95 methanol/dichloromethane). The residue was purified by recrystallization from 1,2-dichloroethane to provide 50 mg of 2-ethyl-1-[3-(thien-2-yl)-2-propynyl]-1H- imidazo[4,5-c]quinolin-4-amine hydroiodide as brown powder, mp 185-205° C. $^1$H NMR (300 MHz, DMSO-$d_6$) δ 13.24 (s, 1H), 8.80 (br, 2H), 8.47 (dd, J=0.9, 8.1 Hz, 1H), 7.86 (dd, J=1.0, 8.4 Hz, 1H), 7.74 (ddd, J=1.1, 7.2, 8.3 Hz, 1H), 7.64 (ddd, J=1.1, 7.2, 8.3 Hz, 1H), 7.61 (dd, J=1.1, 5.0 Hz, 1H), 7.27 (dd, 1.2, 3.7 Hz, 1H), 7.05 (dd, J=3.5, 5.1 Hz, 1H), 5.84 (s, 2H), 3.12 (q, J=7.4 Hz, 2H), 1.42 (t, J=7.4 Hz, 3H); MS (APCI) m/z 333 (M+H)$^+$; Anal. calcd for $C_{19}H_{16}N_4S$·HI: C, 49.59; H, 3.72; N, 12.17. Found: C, 49.86; H, 3.64; N, 12.23.

Example 3

4-[3-(4-Amino-2-ethyl-1H-imidazo[4,5-c]quinolin-1-yl)-1-propynyl]benzonitrile

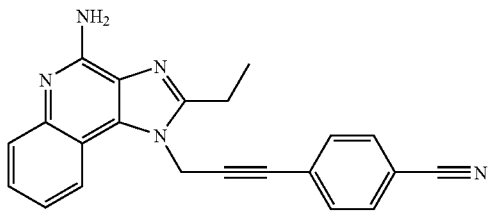 [SMILES: CCc1nc2c(N)nc3ccccc3c2n1CC#Cc1ccc(C#N)cc1]

Tris(dibenzylideneacetone)dipalladium(0) chloroform adduct (62.1 mg, 0.03 eq.), 4-iodobenzonitrile (0.50 g, 0.11 eq.), triethylamine (0.61 g, 3 eq.), and copper (I) iodide (23 mg, 0.06 eq.) were added sequentially to a solution of 2-ethyl-1-(2-propynyl)-1H-imidazo[4,5-c]quinolin-4-amine (0.5 g, 2.0 mmol, 1.0 eq) in DMF. The reaction mixture was stirred at ambient temperature for 3.5 hours. The reaction mixture was concentrated under reduced pressure to provide crude product which was purified by column chromatography (silica gel eluting with 5/95 methanol/dichloromethane). The residue was purified by recrystallization from 1,2-dichloroethane to provide 60 mg of 4-[3-(4-amino-2-ethyl-1H-imidazo[4,5-c]quinolin-1-yl)-1-propynyl]benzonitrile hydroiodide as a brown powder, mp 180-241° C. (dec). $^1$H NMR (300 MHz, DMSO-$d_6$) δ 13.23 (br s, 1H), 8.47 (d, J=8.1 Hz, 1H), 8.44 (br, 2H), 7.82 (m, 3H), 7.69 (t, J=7.2 Hz, 1H), 7.60 (t, J=7.1 Hz, 1H), 7.54 (d, J=8.7 Hz, 2H), 5.84 (s, 2H), 3.13 (q, J=7.4 Hz, 2H), 1.42 (t, J=7.4 Hz, 3H); MS m/z 352 (M+H)$^+$; Anal. calcd for $C_{22}H_{17}N_5$·HI·0.09 1,2-dichloroethane: C, 54.50; H, 3.79; N, 14.33. Found: C, 54.54; H, 3.59; N, 14.26.

Example 4

2-Ethyl-1-(3-phenyl-2-propynyl)-1H-imidazo[4,5-c]quinolin-4-amine

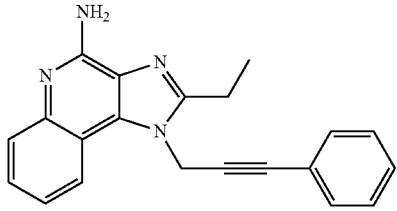 [SMILES: CCc1nc2c(N)nc3ccccc3c2n1CC#Cc1ccccc1]

Tris(dibenzylideneacetone)dipalladium(0) chloroform adduct (62.1 mg, 0.03 eq.), 4-iodobenzene (0.45 g, 1.1 eq.), triethylamine (0.61 g, 3 eq.), and copper (1) iodide (23 mg, 0.06 eq.) were added sequentially to a solution of 2-ethyl-1-(2-propynyl)-1H-imidazo[4,5-c]quinolin-4-amine (0.5 g, 2.0 mmol, 1.0 eq) in DMF. The reaction mixture was stirred at ambient temperature overnight. The reaction mixture was concentrated under reduced pressure to provide crude product which was purified by column chromatography (silica gel eluting with 8/92 methanol/dichloromethane). The residue was purified by recrystallization from 1,2-dichloroethane to provide 60 mg of 2-ethyl-1-(3-phenyl-2-propynyl)-1H-imidazo[4,5-c]quinolin-4-amine hydroiodide as a brown powder, mp 200-212° C. (dec). $^1$H NMR (300 MHz, DMSO-$d_6$) δ 13.25 (s, 1H), 8.79 (br, 2H), 8.53 (dd, J=0.9, 8.5 Hz, 1H), 7.86 (dd, J=0.9, 8.3 Hz, 1H), 7.74 (ddd, J=1.2, 7.2, 8.4 Hz, 1H), 7.66 (ddd, J=1.2, 7.2, 8.3 Hz, 1H), 7.36 (m, 5H), 5.82 (s, 2H), 3.15 (q, J=7.5 Hz, 2H), 1.43 (t, J=7.5 Hz, 3H); MS (APCI) m/z 327 (M+H)$^+$; Anal. Calcd for $C_{21}H_{18}N_4$·HI: C, 55.52; H, 4.22; N, 12.33. Found: C, 55.80; H, 3.94; N, 12.46.

Example 5

2-Ethyl-1-[3-(pyrazin-2-yl)-2-propynyl]-1H-imidazo[4,5-c]quinolin-4-amine

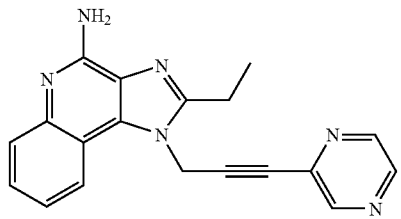 [SMILES: CCc1nc2c(N)nc3ccccc3c2n1CC#Cc1cnccn1]

Tris(dibenzylideneacetone)dipalladium(0) chloroform adduct (0.12 mg, 0.03 eq.), 2-iodopyrazine (0.90 g, 1.1 eq), triethylamine (1.21 g, 3 eq.), and copper (I) iodide (46 mg, 0.06 eq.) were added sequentially to a solution of 2-ethyl-1-(2-propynyl)-1H-imidazo[4,5-c]quinolin-4-amine (1 g, 4 mmol, 1.0 eq.) in DMF. The reaction mixture was stirred at ambient temperature overnight. The reaction mixture was concentrated under reduced pressure to provide crude product which was purified by column chromatography (silica gel eluting with 8/92 methanol/dichloromethane). The residue was purified by recrystallization from DMF to provide 100 mg of 2-ethyl-1-[3-(pyrazin-2-yl)-2-propynyl]-1H-imidazo[4,5-c]quinolin-4-amine hydroiodide as tan granules, mp 180-225° C. (dec). $^1$H NMR (300 MHz, DMSO-$d_6$) δ 13.31 (s, 1H), 8.70 (br s, 2H), 8.68 (d, J=1.4 Hz, 1H), 8.61 (m, 2H), 8.48 (dd, J=8.2, 0.9 Hz, 1H), 7.85 (d, J=8.2 Hz, 1H), 7.73 (m, 1H), 7.62 (m, 1H), 5.93 (s, 2H), 3.14 (q, J=7.4 Hz, 2H), 1.43 (t, J=7.4 Hz, 3H); MS (APCI) m/z 329 (M+H)$^+$; Anal. calcd. for $C_{19}H_{16}N_6$·HI·0.06 DMF: C, 50.01; H, 3.81; N, 18.43. Found: C, 49.96; H, 3.84; N, 18.15.

Example 6

Ethyl 4-[3-(4-Amino-2-ethyl-1H-imidazo[4,5-c]quinolin-1-yl)-1-propynyl]benzoate

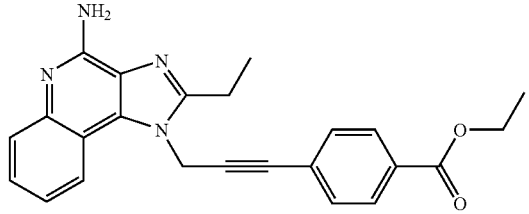 [SMILES: CCOC(=O)c1ccc(C#CCn2c(CC)nc3c(N)nc4ccccc4c32)cc1]

Part A

Tris(dibenzylideneacetone)dipalladium(0) chloroform adduct (65.9 mg, 0.03 eq.), ethyl 4-iodobenzoate (388 μL, 1.1 eq.), triethylamine (887 μL, 3.0 eq.), and copper (I) iodide (24.2 mg, 0.06 eq.) were added sequentially to a solution of 2-ethyl-1-(2-propynyl)-1H-imidazo[4,5-c]quinoline (499 mg, 2.12 mmol, 1.0 eq.) in DMF (10.6 mL). The reaction mixture was stirred at ambient temperature for 1 hour and then concentrated under reduced pressure. The residue was purified by column chromatography (silica gel eluting with 5/95 methanol/chloroform) to provide 0.70 g of ethyl 4-[3-(2-ethyl-1H-imidazo[4,5-c]quinolin-1-yl)-1-propynyl]benzoate as a light tan solid.

Part B

3-Chloroperoxybenzoic acid (0.54 g of 77%, 1.15 eq.) was added in a single portion to a solution of the material from Part A in chloroform (18 mL). The reaction mixture was stirred at ambient temperature for 1.5 hour. The reaction mixture was diluted with chloroform (100 mL), washed with aqueous saturated sodium bicarbonate (2×30 mL), dried over magnesium sulfate and concentrated under reduced pressure to provide 0.70 g of ethyl 4-[3-(2-ethyl-5-oxy-1H-imidazo[4,5-c]quinolin-1-yl)-1-propynyl]benzoate as a white solid.

Part C

Ammonium hydroxide (15 mL) was added to a stirred solution of the material from Part B in chloroform (15 mL). Tosyl chloride (0.37 g, 1.1 eq) was added and the reaction mixture was stirred vigorously for 4 hours. The reaction mixture was diluted with chloroform (30 mL) and the layers were separated. The aqueous layer was back extracted with chloroform (2×20 mL). The combined organics were dried over magnesium sulfate and concentrated under reduced pressure to provide 0.77 g of a light brown solid. This material was triturated with ethyl acetate (10 mL), isolated by filtration and rinsed with ethyl acetate (2×5 mL) to provide 512 mg of a tan solid. This solid was slurried with warm 9/1 acetonitrile/chloroform (~30 mL), cooled to ambient temperature, isolated by filtration and dried under vacuum at 80° C. to provide 0.40 g of ethyl 4-[3-(4-amino-2-ethyl-1H-imidazo[4,5-c]quinolin-1-yl)-1-propynyl]benzoate as a white powder, mp 221-222° C. (dec). $^1$H NMR (300 MHz, DMSO-$d_6$) δ 8.31 (d, J=0.8, 8.1 Hz, 1H), 7.89 (d, J=8.5 Hz, 2H), 7.62 (dd, J=1.0, 8.3 Hz, 1H), 7.49 (d, J=8.5 Hz, 2H), 7.44 (m, 1H), 7.29 (ddd, J=1.3, 7.6, 7.6 Hz, 1H), 6.51 (s, 2H), 5.73 (s, 2H), 4.28 (q, J=7.1 Hz, 2H), 3.06 (q, J=7.5 Hz, 2H), 1.41 (t, J=7.5 Hz, 3H), 1.29 (t, J=7.1 Hz, 3H); MS (APCI) m/z 399 (M+H)$^+$; Anal. Calc. for $C_{24}H_{22}N_4O_2$.0.06 CHCl$_3$: C, 71.24; H, 5.48; N, 13.81. Found: C, 71.02; H, 5.36; N, 13.72.

Example 7

2-Ethyl-1-[3-(4-methoxyphenyl)-2-propynyl]-1H-imidazo[4,5-c]quinolin-4-amine

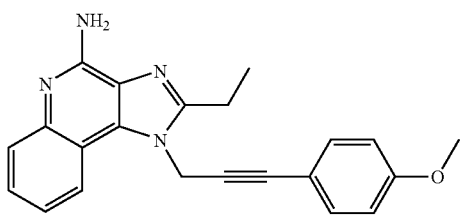 [SMILES: CCc1nc2c(N)nc3ccccc3c2n1CC#Cc1ccc(OC)cc1]

Part A

Tris(dibenzylideneacetone)dipalladium(0) chloroform adduct (64 mg, 0.03 eq.), 4-iodoanisole (531 mg, 1.1 eq.), triethylamine (862 μL, 3.0 eq.), and copper (I) iodide (23.6 mg, 0.06 eq.) were added sequentially to a solution of 2-ethyl-1-(2-propynyl)-1H-imidazo[4,5-c]quinoline (485 mg, 2.06 mmol, 1.0 eq.) in DMF (10 mL). The reaction mixture was stirred at ambient temperature for 3 hour and then concentrated under reduced pressure. The residue was purified by column chromatography (silica gel eluting with 2/98 methanol/chloroform) to provide 0.34 g of 2-ethyl-1-[3-(4-methoxyphenyl)-2-propynyl]-1H-imidazo[4,5-c]quinoline as a clear oil that partially crystallized on standing.

Part B

Using the method of Example 6 Part B, the material from Part A was oxidized to provide 0.32 g of 2-ethyl-1-[3-(4-methoxyphenyl)-2-propynyl]-1H-imidazo[4,5-c]quinolin-5-oxide as a light yellow solid.

Part C

Using the method of Example 6 Part C, the material from Part B was aminated. The crude product was purified by column chromatography (silica gel eluting with 5/95 methanol/chloroform) followed by recrystallization from ethyl acetate to provide 126 mg of 2-ethyl-1-[3-(4-methoxyphenyl)-2-propynyl]-1H-imidazo[4,5-c]quinolin-4-amine as a white powder, mp 179-181° C. $^1$H NMR (300 MHz, DMSO-d6) δ 8.32 (dd, J=1.0, 8.2 Hz, 1H), 7.61 (dd, J=1.0, 8.3 Hz, 1H), 7.44 (ddd, J=1.4, 7.0, 8.3 Hz, 1H), 7.30 (m, 3H), 6.88 (m, 2H), 6.49 (s, 2H), 5.63 (s, 2H), 3.73 (s, 3H), 3.05 (q, J=7.5 Hz, 2H), 1.40 (t, J=7.5 Hz, 3H); MS (APCI) m/z 357 (M+H)$^+$; Anal. calcd for $C_{22}H_{20}N_4O$.0.04$C_4H_8O_2$.0.05$H_2O$: C, 73.76; H, 5.70; N, 15.53. Found: C, 73.47; H, 5.60, N: 15.48; KF: 0.23.

Example 8

2-Ethyl-1-[3-(3-trifluoromethylphenyl)-2-propynyl]-1H-imidazo[4,5-c]quinolin-4-amine

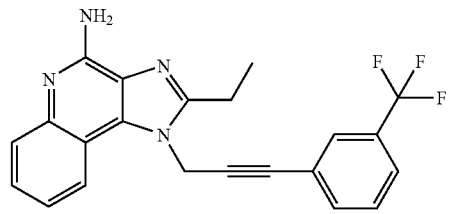 [SMILES: CCc1nc2c(N)nc3ccccc3c2n1CC#Cc1cccc(C(F)(F)F)c1]

Part A

Tris(dibenzylideneacetone)dipalladium(0) chloroform adduct (66 mg, 0.03 eq.), 3-iodobenzotrifluoride (336 μL, 1.1 eq.), triethylamine (889 μL, 3.0 eq.), and copper (I) iodide (24.3 mg, 0.06 eq.) were added sequentially to a solution of 2-ethyl-1-(2-propynyl)-1H-imidazo[4,5-c]quinoline (500 mg, 2.13 mmol, 1.0 eq.) in DMF (10.6 mL). The reaction mixture was stirred at ambient temperature for 1 hour and then concentrated under reduced pressure. The residue was purified by column chromatography (silica gel eluting with 2/98 methanol/chloroform) to provide 0.73 g of 2-ethyl-1-[3-(3-trifluoromethylphenyl)-2-propynyl]-1H-imidazo[4,5-c]quinoline as a light tan solid.

Part B

Using the method of Example 6 Part B, the material from Part A was oxidized to provide 0.69 g of 2-ethyl-1-[3-(3- trifluoromethylphenyl)-2-propynyl]-1H-imidazo[4,5-c]quinoline-5-oxide as a light tan solid.

Part C

Using the method of Example 6 Part C, the material from Part B was aminated. The crude product was purified by trituration with diethyl ether to provide 453 mg of an off white solid. This material was recrystallized sequentially from isopropanol, ethanol, and ethyl acetate to provide 192 mg of 2-ethyl-1-[3-(3-trifluoromethylphenyl)-2-propynyl]-1H-imidazo[4,5-c]quinolin-4-amine as a white powder, mp 202.5-203.5° C. $^1$H NMR (300 MHz, DMSO-$d_6$) δ 8.32 (dd, J=1.0, 8.2 Hz, 1H), 7.63 (m, 5H), 7.44 (ddd, J=1.3, 7.0, 8.3 Hz, 1H), 7.30 (ddd, J=1.3, 7.0, 8.3 Hz, 1H), 6.50 (s, 2H), 5.71 (s, 2H), 3.07 (q, J=7.5 Hz, 2H), 1.41 (t, J=7.5 Hz, 3H); MS (APCI) m/z 395 (M+H)$^+$; Anal. calcd for $C_{22}H_{17}F_3N_4$: C, 67.00; H, 4.34; N, 14.21. Found: C, 66.74; H, 4.00; N, 14.19.

Example 9

2-Ethyl-1-[3-(2-trifluoromethylphenyl)-2-propynyl]-1H-imidazo[4,5-c]quinolin-4-amine

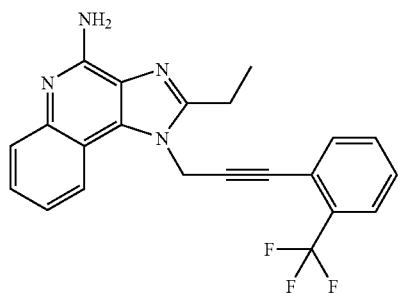 [SMILES: CCc1nc2c(N)nc3ccccc3c2n1CC#Cc1ccccc1C(F)(F)F]

Part A

Tris(dibenzylideneacetone)dipalladium(0) chloroform adduct (64.5 mg, 0.03 eq.), 2-iodobenzotrifluoride (321 μL, 1.1 eq.), triethylamine (869 μL, 3.0 eq.), and copper (I) iodide (23.7 mg, 0.06 eq.) were added sequentially to a solution of 2-ethyl-1-(2-propynyl)-1H-imidazo[4,5-c]quinoline (489 mg, 2.08 mmol, 1.0 eq.) in DMF (10.6 mL). The reaction mixture was stirred at ambient temperature for 18 hours and then concentrated under reduced pressure. The residue was purified by column chromatography (silica gel eluting with 3/97 methanol/chloroform) to provide 0.13 g of 2-ethyl-1-[3-(2-trifluoromethylphenyl)-2-propynyl]-1H-imidazo[4,5-c]quinoline as a light yellow solid.

Part B

3-Chloroperoxybenzoic acid (93 mg of 77%, 1.1 eq.) was added in a single portion to a solution of the material from Part A in chloroform (3.4 mL). The reaction mixture was stirred at ambient temperature for 45 minutes at which time analysis by TLC indicated that the oxidation was complete. Ammonium hydroxide (3 mL) was added followed by tosyl chloride (75 mg, 1.15 eq). The reaction mixture was stirred vigorously for 1 hour and then diluted with chloroform (3 mL) and water (3 mL). The layers were separated and the aqueous layer was back extracted with chloroform (2×10 mL). The combined organics were dried over magnesium sulfate and then concentrated under reduced pressure to provide 0.14 g of a tan solid. This material was triturated with hot ethyl acetate (~12 mL), cooled to ambient temperature, isolated by filtration and rinsed with ethyl acetate (2×2 mL) to provide 56 mg of a light tan solid. This material was recrystallized from 1,2-dichloromethane and then dried under vacuum at 80° C. to provide 29 mg of 2-ethyl-1-[3-(2-trifluoromethylphenyl)-2-propynyl]-1H-imidazo[4,5-c]quinolin-4-amine as colorless crystals, mp 234-235° C. (dec.). $^1$H NMR (300 MHz, DMSO-$d_6$) δ 8.28 (d, J=7.4 Hz, 1H), 7.73 (d, J=7.7 Hz, 1H), 7.60 (m, 4H), 7.43 (ddd, J=1.3, 7.0, 8.3 Hz, 1H), 7.25 (ddd, J=1.3, 7.0, 8.2 Hz, 1H), 6.49 (s, 2H), 5.74 (s, 2H), 3.06 (q, J=7.5 Hz, 2H), 1.40 (t, J=7.5 Hz, 3H); MS (APCI) m/z 395 (M+H)$^+$; Anal. calcd for $C_{22}H_{17}F_3N_4 \cdot 0.05 C_2H_4Cl_2$: C, 66.47; H, 4.34; N, 14.03. Found: C, 66.10; H, 4.44; N, 13.89.

Example 10

2-Ethyl-1-[3-(4-nitrophenyl)-2-propynyl]-1H-imidazo[4,5-c]quinolin-4-amine

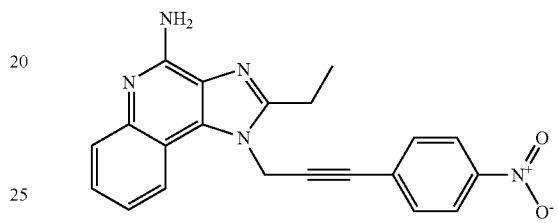

Part A

Tris(dibenzylideneacetone)dipalladium(0) chloroform adduct (95 mg, 0.03 eq.), 4-iodonitrobenzene (0.84 g, 1.1 eq.), triethylamine (0.92 g, 3 eq.), and copper (I) iodide (35 mg, 0.06 eq.) were added sequentially to a solution of 2-ethyl-1-(2-propynyl)-1H-imidazo[4,5-c]quinolin-4-amine (0.72 g, 3.0 mmol, 1.0 eq.) in DMF. The reaction mixture was stirred at ambient temperature overnight. The reaction mixture was concentrated under reduced pressure and the residue was partitioned between dichloromethane (30 mL) and water (50 mL). The organic layer was separated, washed twice with water, and then concentrated under reduced pressure to a solid. This material was purified by column chromatography (silica gel eluting with 3/97 methanol/dichloromethane) to provide 0.4 g of 2-ethyl-1-[3-(4-nitrophenyl)-2-propynyl]-1H-imidazo[4,5-c]quinoline.

Part B

3-Chloroperoxybenzoic acid (0.365 g of 70%, 1.1 eq) was added in portions to a solution of the material from Part A in dichloromethane. When analysis by TLC indicated that the oxidation was complete, excess concentrated ammonium hydroxide was added and the reaction mixture was stirred vigorously. Tosyl chloride (0.262 mg, 1.1 eq.) was added in portions and the reaction mixture was stirred at ambient temperature for 1 hour. The organic layer was separated, washed sequentially with 5% sodium carbonate (2×50 mL) and water (50 mL), and concentrated under reduced pressure to provide 0.6 g of crude product as an oil. This oil was purified by column chromatography (silica gel eluting sequentially with dichloromethane and 2/98 methanol/dichloromethane) followed by recrystallization from dichloromethane to provide 16 mg of 2-ethyl-1-[3-(4-nitrophenyl)-2-propynyl]-1H-imidazo[4,5-c]quinolin-4-amine as a yellow granular solid, mp 190-206° C. $^1$H NMR (300 MHz, DMSO-$d_6$) δ 8.30 (dd, J=8.1, 1.1 Hz, 1H), 8.17 (d, J=8.9 Hz, 2H), 7.62 (m, 3H), 7.44 (ddd, J=1.4, 7.0, 8.3 Hz, 1H), 7.29 (ddd, J=1.4, 7.0, 8.3 Hz, 1H), 6.51 (s, 2H), 5.77 (s, 2H), 3.07 (q, J=7.4 Hz, 2H), 1.40 (t, J=7.4 Hz, 3H); MS (APCI) m/z 372 (M+H)$^+$; Anal. calcd for $C_{21}H_{17}N_5O_2 \cdot 0.5 H_2O$: C, 66.31; H, 4.77; N, 18.41. Found: C, 66.13; H, 4.61; N, 18.21.

Example 11

2-Ethyl-1-[3-(3-nitrophenyl)-2-propynyl]-1H-imidazo[4,5-c]quinolin-4-amine

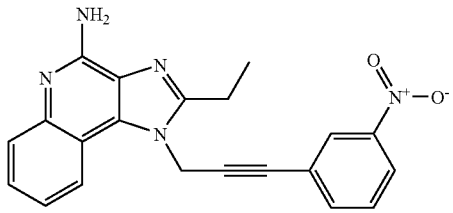 [SMILES: CCc1nc2c(N)nc3ccccc3c2n1CC#Cc1cccc([N+](=O)[O-])c1]

Part A

Tris(dibenzylideneacetone)dipalladium(0) chloroform adduct (0.395 mg, 0.03 eq.), 3-iodonitrobenzene (3.5 g, 1.1 eq.), triethylamine (3.87 g, 3 eq.), and copper (I) iodide (0.145 g, 0.06 eq.) were added sequentially to a solution of 2-ethyl-1-(2-propynyl)-1H-imidazo[4,5-c]quinolin-4-amine (3 g, 13 mmol, 1.0 eq.) in DMF. The reaction mixture was stirred at ambient temperature for 3.5 hours. A precipitate was isolated by filtration and then recrystallized from dichloromethane to provide 2.6 g of 2-ethyl-1-[3-(3-nitrophenyl)-2-propynyl]-1H-imidazo[4,5-c]quinoline as a solid.

Part B

3-Chloroperoxybenzoic acid (1.38 g, 1.1. eq.) was added in portions to a solution of the material from Part A in dichloromethane (25 mL). Two additional portions (0.25 eq. each) of 3-chloroperoxybenzoic acid were added at ½ hour and 1 hour. The reaction mixture was filtered to remove some black material. Concentrated ammonium hydroxide (20 mL) was added to the filtrate. Tosyl chloride (1.53 g, 1.1 eq.) was added in portions with vigorous stirring. A precipitate was isolated by filtration, recrystallized from N-methylpyrrolidine and dried under vacuum at 80° C. to provide 0.2 g of 2-ethyl-1-[3-(3-nitrophenyl)-2-propynyl]-1H-imidazo[4,5-c]quinoline-4-amine as yellow powder, mp 224-243° C. $^1$H NMR (300 MHz, TFA-d) δ 8.76 (d, J=8.6 Hz, 1H), 8.31 (m, 2H), 8.08 (t, J=8.3 Hz, 1H), 7.96 (m, 2H), 7.79 (dd, J=1.2, 7.8 Hz, 1H), 7.60 (t, J=8.1 Hz, 1H), 5.94 (s, 2H), 3.62 (q, J=7.4 Hz, 2H), 1.80 (t, J=7.4 Hz, 3H). MS (APCI) m/z 372 (M+H)$^+$; Anal. calcd for $C_{21}H_{17}N_5O_2$·0.03 DMF: C, 67.35; H, 4.77; N, 18.87. Found: C, 67.33; H, 4.77; N, 18.92.

Example 12

2-Ethyl-1-[5-(thien-2-yl)-4-pentynyl]-1H-imidazo[4,5-c]quinolin-4-amine

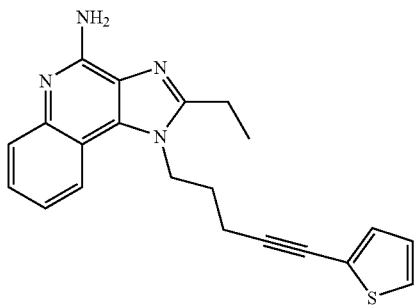 [SMILES: CCc1nc2c(N)nc3ccccc3c2n1CCCC#Cc1cccs1]

Part A

Triethylamine (11.8 g, 1.1 eq.) was added to a suspension of 4-chloro-3-nitroquinoline (20 g, 48 mmol. 1.0 eq.) in dichloromethane (200 mL). A solution of 4-aminobutan-1-ol (9.6 g, 1.1 eq.) in dichloromethane (50 mL) was added dropwise. The reaction mixture was stirred for 2 hours and then concentrated under reduced pressure. The residue was triturated with water. The resulting solid was isolated by filtration, air dried, and purified by chromatography (silica gel eluting sequentially with dichloromethane and 5/95 methanol/dichloromethane) to provide 24.2 g of 4-[(3-nitroquinolin-4-yl)amino]butan-1-ol.

Part B

Catalyst (5% Pd/C) was added to a suspension of 4-[(3-nitroquinolin-4-yl)amino]butan-1-ol (18.2 g, 69.6 mmol) in toluene (450 mL) in a Parr vessel. The vessel was placed on a shaker and pressurized with hydrogen. The next day ethanol (60 mL) and additional catalyst were added and the vessel was again pressurized with hydrogen. After 1 hour analysis by TLC indicated that all of the starting material had been consumed. The reaction mixture was filtered through a layer of CELITE filter aid and then concentrated under reduced pressure to provide 17 g of 4-[(3-aminoquinolin-4-yl)amino]butan-1-ol.

Part C

Triethyl orthopropionate (15.1 mL of 97%, 1.1 eq.) and a catalytic amount of pyridine hydrochloride were added to a solution of 4-[(3-aminoquinolin-4-yl)amino]butan-1-ol (16 g, 69 mmol, 1 eq.) in pyridine (150 mL). The reaction mixture was refluxed for 1 hour at which time analysis by TLC indicated that all of the starting material had been consumed. The reaction mixture was concentrated under reduced pressure and the residue was triturated with water (300 mL). The resulting solid was isolated by filtration and then recrystallized from ethyl acetate to provide 8.2 g of 4-(2-ethyl-1H-imidazo[4,5-c]quinolin-1-yl)butan-1-ol. A second crop (1.9 g) was obtained by reducing the volume of the mother liquor.

Part D

Under a nitrogen atmosphere, dimethylsulfoxide (3.6 mL, 1.5 eq.) and oxalyl chloride (3.5 mL, 1.1 eq.) were sequentially added dropwise to chilled (dry ice/acetone bath) dichloromethane (100 mL). A solution of 4-(2-ethyl-1H-imidazo[4,5-c]quinolin-1-yl)butan-1-ol (10 g, 37 mmol, 1 eq.) in dichloromethane was added dropwise. Triethylamine (15.5 mL, 3 eq.) was added. The ice bath was removed and the reaction mixture was allowed to warm to ambient temperature. After about 2 hours analysis by TLC indicated that the reaction was complete. The reaction mixture was diluted with dichloromethane (175 mL) and water (200 mL) and made basic (pH 10) with aqueous 5% sodium carbonate. The organic layer was washed sequentially with water (2×200 mL) and brine (150 mL) and then concentrated under reduced pressure to provide 9.9 g of 4-(2-ethyl-1H-imidazo[4,5-c]quinolin-1-yl)butanal.

Part E

Diethyl 1-diazo-2-oxopropylphosphonate (9.6 g, 1.2 eq.) was added to a solution of 4-(2-ethyl-1H-imidazo[4,5-c]quinolin-1-yl)butanal (11.15 g, 41.7 mmol, 1 eq.) and potassium carbonate (11.6 g, 2 eq.) in methanol. The reaction mixture was stirred until analysis by TLC indicated that all of the starting material had been consumed. The reaction mixture was filtered and the filter cake was rinsed until clear. The filtrate was concentrated under reduced pressure to provide crude product as an oil. The oil was partitioned between dichloromethane (200 mL) and water (100 mL). The organic layer was washed sequentially with water and brine (2×100 mL) and then concentrated under reduced pressure to provide 8.8 g of 2-ethyl-1-(4-pentynyl)-1H-imidazo[4,5-c]quinoline.

Part F

3-Chloroperoxybenzoic acid (8.0 g of 65%, 1.1 eq.) was added in portions to a solution of 2-ethyl-1-(4-pentynyl)-1H-imidazo[4,5-c]quinoline (7.2 g, 27 mmol, 1 eq.) in dichloromethane (70 mL). After 1 hour analysis by TLC indicated that the starting material had been consumed. The reaction mixture was washed sequentially with aqueous 5% sodium carbonate (3×100 mL), water (100 mL) and ammonium hydroxide. The organic layer was combined with 15 M ammonium hydroxide (60 mL). Tosyl chloride (5.74 g, 1.1 eq.) was added in portions with vigorous stirring. After ½ hour analysis by TLC indicated that the reaction was complete. The reaction mixture was filtered to remove a precipitate. The filtrate was diluted with dichloromethane ((100 mL). The organic layer was washed with 10% sodium hydroxide and concentrated under reduced pressure. The residue was recrystallized from a mixture of aqueous ethanol, a few drops of 10% sodium hydroxide and 1,2-dichloroethane to provide 2-ethyl-1-(4-pentynyl)-1H-imidazo[4,5-c]quinolin-4-amine as beige plates, mp 219.0-223.0° C. $^1$H NMR (300 MHz, CDCl$_3$) δ 8.01 (dd, J=8.2, 0.9 Hz, 1H), 7.79 (dd, J=8.4, 0.9 Hz, 1H), 7.50 (ddd, J=8.4, 7.0, 1.4 Hz, 1H), 7.30 (dt, J=8.3, 7.0, 1.4 Hz, 1H), 4.58 (t, J=7.9 Hz, 2H), 2.98 (q, J=7.4 Hz, 2H), 2.39 (m, 2H), 2.15 (m, 3H), 1.49 (t, J=7.4 Hz, 3H); MS (APCI) m/z 279 (M+H)$^+$; Anal. calcd for C$_{17}$H$_{18}$N$_4$.0.07C$_2$H$_6$O: C, 73.11; H, 6.59; N, 19.90. Found: C, 73.10; H, 6.68; N, 19.91.

Part G

Tris(dibenzylideneacetone)dipalladium(0) chloroform adduct (0.112 g, 0.03 eq.), 2-iodothiophene (3.9 g, 1.1 eq.), triethylamine (1.1 g, 3 eq.), and copper (I) iodide (0.042 g, 0.06 eq.) were added sequentially to a solution of 2-ethyl-1-(4-pentynyl)-1H-imidazo[4,5-c]quinolin-4-amine (1.0 g, 3.5 mmol, 1.0 eq.) in dichloromethane (20 mL). The reaction mixture was stirred at ambient temperature for 6 hours at which time analysis by liquid chromatography/mass spectroscopy indicated that the reaction was complete. The reaction mixture was absorbed onto the top of a column of silica gel (30 g) and the column was eluted sequentially with dichloromethane and 3/97 methanol/dichloromethane. The product was recrystallized from 1,2-dichloroethane to provide 0.25 g of 2-ethyl-1-[5-(thien-2-yl)-4-pentynyl]-1H-imidazo[4,5-c]quinolin-4-amine as an off white powder, mp 175.0-190.0° C. (dec.). $^1$H NMR (300 MHz, CDCl$_3$) δ 8.09 (dd, J=8.3, 1.0 Hz, 1H), 7.82 (dd, J=8.3, 1.0 Hz, 1H), 7.48 (ddd, J=8.4, 6.9, 1.3 Hz, 1H), 7.24 (m, 3H), 6.99 (dd, J=5.1, 3.6 Hz, 1H), 5.37 (s, 2H), 4.65 (t, J=7.7 Hz, 2H), 3.01 (q, J=7.5 Hz, 2H), 2.63 (t, J=6.2 Hz, 2H), 2.23 (m, 2H), 1.49 (t, J=7.4 Hz, 3H); MS (APCI) m/z 361 (M+H)$^+$; Anal. calcd for C$_{21}$H$_{20}$N$_4$S.0.03C$_2$H$_4$Cl$_2$: C, 69.88; H, 5.59; N, 15.51. Found: C, 69.59; H, 5.69; N, 15.34.

Example 13

2-Ethyl-1-[5-(pyridin-2-yl)-4-pentynyl]-1H-imidazo[4,5-c]quinolin-4-amine

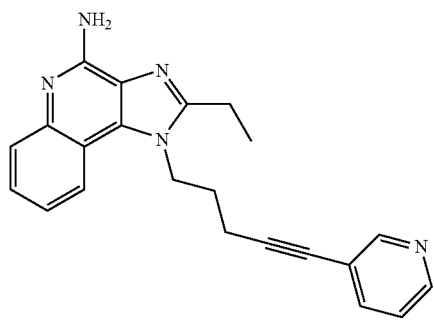 [SMILES: CCc1nc2c(N)nc3ccccc3c2n1CCCC#Cc1cccnc1]

Tris(dibenzylideneacetone)dipalladium(0) chloroform adduct (0.095 g, 0.03 eq.), 3-iodopyridine (0.626 g, 1.1 eq.), triethylamine (0.923 g, 3 eq.), and copper (I) iodide (0.035 g, 0.06 eq.) were added sequentially to a solution of 2-ethyl-1-(4-pentynyl) 1H-imidazo[4,5-c]quinolin-4-amine (0.85 g, 3.0 mmol, 1.0 eq.) in DMF. The reaction mixture was stirred for 1 hour and then concentrated under reduced pressure. The residue was purified by column chromatography (silica gel eluting with 4/96 methanol/dichloromethane). The product was recrystallized from a mixture of ethanol and 1,2-dichloroethane. The resulting solid was dissolved in 1:1 mixture of ethanol and 1,2-dichloroethane, treated with activated charcoal, combined with a few drops of 10% sodium hydroxide, heated and then filtered while still hot. The filtrate was concentrated under reduced pressure to provide 0.2 g of 2-ethyl-1-[5-(pyridin-2-yl)-4-pentynyl]-1H-imidazo[4,5-c]quinolin-4-amine as light brown granules, mp 188.0-192.0° C. $^1$H NMR (300 MHz, CDCl$_3$) δ 8.70 (d, J=0.9 Hz, 1H), 8.55 (dd, J=4.7, 1.3 Hz, 1H), 8.06 (dd, J=8.2, 0.9 Hz, 1H), 7.82 (dd, J=8.4, 0.7 Hz, 1H), 7.71 (ddd, J=7.9, 1.7, 1.7 Hz, 1H), 7.48 (ddd, J=8.3, 7.2, 1.2 Hz, 1H), 7.25 (m, 2H), 5.46 (br s, 2H), 4.66 (t, J=7.9 Hz, 2H), 3.00 (q, J=7.4 Hz, 2H), 2.64 (t, J=6.5 Hz, 2H), 2.26 (m, 2H), 1.49 (t, J=7.4 Hz, 3H); MS (APCI) m/z 356 (M+H)$^+$; Anal. calcd for C$_{22}$H$_{21}$N$_5$.0.65H$_2$O: C, 71.97; H, 6.12; N, 19.07. Found: C, 72.03; H, 6.06; N, 19.16.

Example 14

2-Ethyl-1-[5-(4-methoxyphenyl)-4-pentynyl]-1H-imidazo[4,5-c]quinolin-4-amine

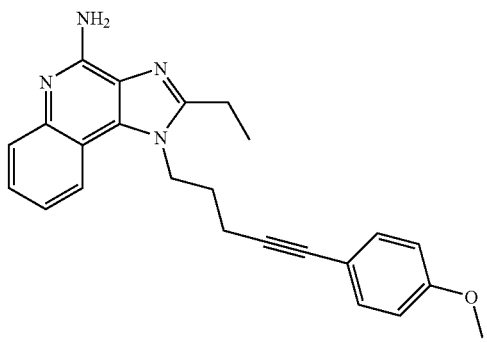 [SMILES: CCc1nc2c(N)nc3ccccc3c2n1CCCC#Cc1ccc(OC)cc1]

Tris(dibenzylideneacetone)dipalladium(0) chloroform adduct (0.095 g, 0.03 eq.), 4-iodoanisole (0.786 g, 1.1 eq.), triethylamine (1.3 mL, 3 eq.), and copper (I) iodide (0.035 g, 0.06 eq.) were added sequentially to a solution of 2-ethyl-1-(4-pentynyl)-1H-imidazo[4,5-c]quinolin-4-amine (0.85 g, 3.0 mmol, 1.0 eq.) in DMF. The reaction mixture was stirred for about 4 hours and then concentrated under reduced pressure. The residue was purified by column chromatography (silica gel eluting with 4/96 methanol/dichloromethane) to provide an oil. The oil was recrystallized from ethanol to provide 2-ethyl-1-[5-(4-methoxyphenyl)-4-pentynyl]-1H-imidazo[4,5-c]quinolin-4-amine hydroiodide as off white granules, mp 230.0° C. $^1$H NMR (300 MHz, DMSO-d$_6$) δ 13.14 (broad s, 1H), 8.65 (broad s, 2H), 8.37 (d, J=8.6 Hz, 1H), 7.83 (dd, J=8.4, 0.8 Hz, 1H), 7.68 (t, J=7.4 Hz, 1H), 7.41 (dt, J=8.1, 0.7 Hz, 1H), 7.34 (m, 2H), 6.93 (m, 2H), 4.73 (t, J=7.5 Hz, 2H), 3.77 (s, 3H), 3.08 (q, J=7.4 Hz, 2H), 2.66 (t, J=6.9 Hz, 2H), 2.09 (m, 2H), 1.41 (t, J=7.4 Hz, 3H); MS (APCI) m/z 385 (M+H)$^+$; Anal. calcd for C$_{24}$H$_{24}$N$_4$O$_1$.HI.0.08C$_2$H$_4$Cl$_2$: C, 55.30; H, 4.89; N, 10.69. Found: C, 55.39; H, 4.88; N, 10.63.

Example 15

2-Ethyl-1-(5-phenyl-4-pentynyl)-1H-imidazo[4,5-c]quinolin-4-amine

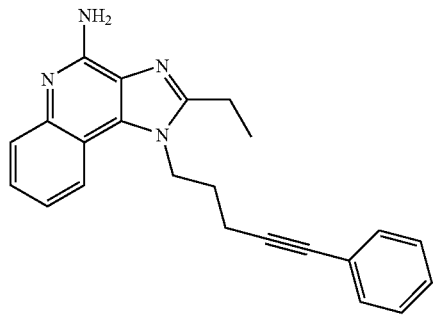 [SMILES: CCc1nc2c(N)nc3ccccc3c2n1CCCC#Cc1ccccc1]

Tris(dibenzylideneacetone)dipalladium(0) chloroform adduct (0.095 g, 0.03 eq.), iodobenzene (0.685 g, 1.1 eq.), triethylamine (0.923 g, 3 eq.), and copper (I) iodide (0.035 g, 0.06 eq.) were added sequentially to a solution of 2-ethyl-1-(4-pentynyl)-1H-imidazo[4,5-c]quinolin-4-amine (0.85 g, 3.0 mmol, 1.0 eq.) in DMF. The reaction mixture was stirred for 1 hour and then concentrated under reduced pressure. The residue was purified by column chromatography (silica gel eluting with 4/96 methanol/dichloromethane) to provide an oil. The oil was recrystallized from a mixture of ethanol and 1,2-dichloroethane. The resulting solid was dissolved in 1:1 mixture of ethanol and 1,2-dichloroethane, treated with activated charcoal, combined with a few drops of 10% sodium hydroxide, heated, and then filtered while still hot. The filtrate was concentrated under reduced pressure to provide 0.28 g of 2-ethyl-1-(5-phenyl-4-pentynyl)-1H-imidazo[4,5-c]quinolin-4-amine as white granules, mp 199.0-202.0° C. $^1$H NMR (300 MHz, DMSO-$d_6$) δ 8.18 (dd, J=8.2, 1.0 Hz, 1H), 7.60 (dd, J=8.3, 0.9 Hz, 1H), 7.35-7.48 (m, 6H), 7.09 (ddd, J=8.2, 7.1, 1.2 Hz, 1H), 6.46 (s, 2H), 4.61 (t, J=7.8 Hz, 2H), 3.01 (q, J=7.4 Hz, 2H), 2.66 (t, J=6.5 Hz, 2H), 2.09 (m, 2H), 1.38 (t, J=7.4 Hz, 3H); MS (APCI) m/z 355 (M+H)$^+$; Anal. calcd for $C_{23}H_{22}N_4 \cdot 0.02C_2H_4Cl_2$: C, 77.64; H, 6.24; N, 15.72. Found: C, 77.68; H, 6.19; N, 15.64.

Example 16

2-Ethyl-1-[5-(3-trifluoromethylphenyl)-4-pentynyl]-1H-imidazo[4,5-c]quinolin-4-amine

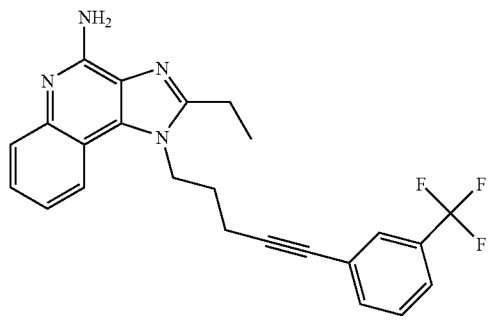 [SMILES: CCc1nc2c(N)nc3ccccc3c2n1CCCC#Cc1cccc(C(F)(F)F)c1]

Tris(dibenzylideneacetone)dipalladium(0) chloroform adduct (0.095 g, 0.03 eq.), 3-iodobenzotrifluoride (0.91 g, 1.1 eq.), triethylamine (0.923 g, 3 eq.), and copper (I) iodide (0.035 g, 0.06 eq.) were added sequentially to a solution of 2-ethyl-1-(4-pentynyl) 1H-imidazo[4,5-c]quinolin-4-amine (0.85 g, 3.0 mmol, 1.0 eq.) in DMF. The reaction mixture was stirred for 1.5 hours and then concentrated under reduced pressure. The residue was partitioned between dichloromethane (50 mL) and water (50 mL). The organic layer was washed sequentially with water (3×30 mL) and brine and then concentrated under reduced pressure. H NMR of the residue showed the presence of DMF so the partitioning, washing and concentrating procedure was repeated to provide 0.7 g of a bright yellow solid. This solid was triturated with hot methanol to provide a white solid. This solid was recrystallized from aqueous ethanol containing several drops of 10% sodium hydroxide to provide 2-ethyl-1-[5-(3-trifluoromethylphenyl)-4-pentynyl]-1H-imidazo[4,5-c]quinolin-4-amine as off white granules, mp 178.0-181.0° C. $^1$H NMR (300 MHz, DMSO-$d_6$) δ 8.19 (d, J=8.4 Hz, 1H), 7.79 (s, 1H), 7.74 (d, J=8.4 Hz, 2H), 7.63 (t, J=7.9 Hz, 2H), 7.38 (broad s, 1H), 7.08 (m, 1H), 6.45 (broad s, 2H), 4.68 (t, J=7.8 Hz, 2H), 3.01 (q, J=7.4 Hz, 2H), 2.70 (t, J=6.7 Hz, 2H), 2.10 (m, 2H), 1.38 (t, J=7.4 Hz, 3H); MS (APCI) m/z 423 (M+H)$^+$; Anal. calcd for $C_{24}H_{21}F_3N_4 \cdot 0.27H_2O$: C, 67.46; H, 5.08; N, 13.11. Found: C, 67.34; H, 4.75; N, 13.11.

Example 17

(E)-2-Ethyl-1-[5-(pyridin-3-yl)-4-pentenyl]-1H-imidazo[4,5-c]quinolin-4-amine

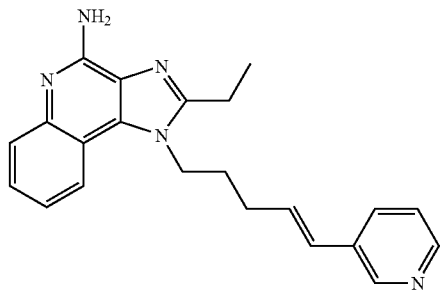 [SMILES: CCc1nc2c(N)nc3ccccc3c2n1CCC/C=C/c1cccnc1]

Part A

Bis(cyclopentadienyl)zirconium chloride hydride (20.57 g, 2.2 eq.) was added in two portions to a stirred solution of 2-ethyl-1-(4-pentynyl)-1H-imidazo[4,5-c]quinoline (9.55 g, 36.3 mmol, 1.0 eq.) in dichloromethane (180 mL). The reaction mixture was cooled for several minutes in an ice bath. After 45 minutes analysis by high performance liquid chromatography (HPLC) indicated that the reaction was complete. Solid iodine (11.04 g, 1.2 eq.) was added in a single portion. The reaction mixture was stirred for 1 hour and then combined with water (100 mL) and sodium sulfate (1 g). The reaction mixture was stirred for several minutes and then poured into a mixture of water (400 mL) and chloroform (200 mL). The mixture was made basic (pH ~8-9) with 10% sodium hydroxide. The organic layer was separated and the aqueous layer was extracted with chloroform (2×200 mL). The combined organics were dried over magnesium sulfate, filtered through a layer of CELITE filter aid, and then concentrated under reduced pressure to provide 15.6 g of brown foam. This material was purified on a HORIZON High-Performance Flash Chromatography instrument (available from Biotage, Inc, Charlottesville, Va., USA) (silica gel eluting with a gradient of 4/96 to 11/89 methanol/chloroform) to provide 10.5 g of brown solid. This material was triturated with acetonitrile (~75 mL), isolated by filtration, rinsed with acetonitrile (2×20 mL) and dried under vacuum to provide 7.21 g of (E)-2-ethyl-1-(5-iodo-4-pentenyl)-1H-imidazo[4,5-c]quinoline as a tan solid.

Part B

3-Chloroperoxy benzoic acid (5.44 g of 77%, 1.2 eq.) was added to a solution of the material from Part A in chloroform (180 mL). After 45 minutes additional 3-chloroperoxybenzoic acid (0.15 eq.) was added and the reaction mixture was stirred for 1 hour. Ammonium hydroxide (60 mL) and tosyl chloride (4.38 g, 1.25 eq.) were added in a single portion and the reaction mixture was stirred for 3 hours. The layers were separated and the aqueous layer was extracted with chloroform (1×50 mL). The combined organics were dried over magnesium sulfate and then concentrated under reduced pressure to provide 10.07 g of brown solid. This material was triturated with acetonitrile (~50 mL), isolated by filtration, rinsed with acetonitrile (2×20 mL) and dried under vacuum to provide 5.56 g of (E)-2-ethyl-1-(5-iodo-4-pentenyl)-1H-imidazo[4,5-c]quinolin-4-amine as a tan solid.

Part C

Water (4 mL), 3-pyridineboronic acid, 1,3-propanediol cyclic ester (450 mg, 1.4 eq.), triphenylphosphine (31 mg, 0.06 eq.), palladium (II) acetate (9 mg, 0.02 eq.), and 2 M aqueous sodium carbonate (2.95 mL, 3.0 eq.) were added to a stirred suspension of (E)-2-ethyl-1-(5-iodo-4-pentenyl)-1H-imidazo[4,5-c]quinolin-4-amine (800 mg, 1.97 mmol, 1.0 eq.) in ethanol (16 mL). The resulting suspension was heated at 70° C. under nitrogen for 21 hours. Additional palladium (II) acetate (0.01 eq.) was added and the reaction mixture was heated for an additional 3 hours. The reaction mixture was cooled to ambient temperature and the bulk of the ethanol was removed under reduced pressure. The residue was partitioned between dichloromethane (150 mL) and water (150 mL). The aqueous layer was back extracted with dichloromethane (2×50 mL). The combined organics were dried over magnesium sulfate and then concentrated under reduced pressure to provide 0.66 of tan foam. This material was purified on a HORIZON High-Performance Flash Chromatography instrument (silica gel eluting with 0-20% 80/18/2 chloroform/methanol/ammonium hydroxide (CMA) in dichloromethane for 672 mL and 20-30% CMA in dichloromethane for 192 mL to provide 212 mg of a white solid which was dried at 60° C. for 16 hours to provide (E)-2-ethyl-1-[5-(pyridin-3-yl)-4-pentenyl]-1H-imidazo[4,5-c]quinolin-4-amine as a white powder, mp 188-190° C. $^1$H NMR (300 MHz, DMSO-d$_6$) δ 8.59 (d, J=1.6 Hz, 1H), 8.40 (dd, J=1.6, 4.8 Hz, 1H), 8.04 (d, J=7.6 Hz, 1H), 7.84 (ddd, J=1.9, 1.9, 7.8 Hz, 1H), 7.60 (dd, J=1.2, 7.2, 8.3 Hz, 1H), 7.40 (ddd, J=1.2, 7.2, 8.3 Hz, 1H), 7.33 (dd, J=4.8, 8.1 Hz, 1H), 7.17 (ddd, J=1.2, 7.2, 8.3 Hz, 1H), 6.47 (m, 4H), 4.57 (t, J=7.5 Hz, 2H), 2.97 (q, J=7.5 Hz, 2H), 2.39 (m, 2H), 2.01 (m, 2H), 1.38 (t, J=7.5 Hz, 3H); MS (APCI) m/z 358 (M+H)$^+$; Anal. calcd for $C_{22}H_{23}N_5$: C, 73.92; H, 6.49; N, 19.59. Found: C, 73.60; H, 6.27; N, 19.37.

Example 18

(E)-2-Ethyl-1-[5-(4-methoxyphenyl)-4-pentenyl]-1H-imidazo[4,5-c]quinolin-4-amine

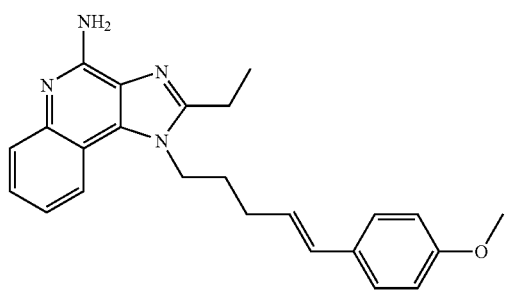 [SMILES: CCc1nc2c(N)nc3ccccc3c2n1CCC/C=C/c1ccc(OC)cc1]

Water (0.1 mL), 4-methoxyphenylboronic acid (449 mg, 1.2 eq.), triphenylphosphine (39 mg, 0.06 eq.), palladium (II) acetate (11 mg, 0.02 eq.), and 2 M aqueous sodium carbonate (3.7 mL, 3.0 eq.) were added to a stirred suspension of (E)-2-ethyl-1-(5-iodo-4-pentenyl)-1H-imidazo[4,5-c]quinolin-4-amine (1.00 g mg, 2.46 mmol, 1.0 eq.) in ethanol (0.5 mL). The resulting suspension was heated at 70° C. under nitrogen for 4.5 hours. Additional triphenylphosphine (0.05 eq.), palladium (II) acetate (0.02 eq.) and 4-methoxyphenylboronic acid (0.3 eq.) were added and the reaction mixture was stirred for another 5 hours. The reaction mixture was cooled to ambient temperature and the bulk of the ethanol was removed under reduced pressure. The residue was partitioned between dichloromethane (100 mL) and water (50 mL). The aqueous layer was back extracted with dichloromethane (1×50 mL). The combined organics were dried over magnesium sulfate and then concentrated under reduced pressure to provide 1.11 g of brown foam. This material was purified on a HORIZON High-Performance Flash Chromatography instrument (silica gel eluting with 0-10% CMA in dichloromethane over 480 mL, 10% CMA in dichloromethane over 380 mL, 10-20% CMA in dichloromethane over 192 mL, 20-30% CMA in dichloromethane over 192 mL, and 30% CMA in dichloromethane for 210 mL) to provide 0.44 g of white solid. This material was recrystallized from ethanol (~10 mL) to provide 294 mg of (E)-2-ethyl-1-[5-(4-methoxyphenyl)-4-pentenyl]-1H-imidazo[4,5-c]quinolin-4-amine as a white powder, mp 179-180° C. $^1$H NMR (300 MHz, DMSO-d$_6$) δ 8.04 (d, J=8.0 Hz, 1H), 7.60 (d, J=8.4 Hz, 1H), 7.40 (m, 1H), 7.34 (d, J=8.6 Hz, 2H), 7.17 (t, J=8.6 Hz, 1H), 6.88 (d, J=8.6 Hz, 2H), 6.44 (br s, 2H), 6.40 (d, J=15.8 Hz, 1H), 6.19 (ddd, J=6.4, 6.4, 15.8 Hz, 1H), 4.54 (t, J=7.6 Hz, 2H), 3.74 (s, 3H), 2.96 (q, J=7.6 Hz, 2H), 2.34 (m, 2H), 1.98 (m, 2H), 1.37 (t, J=7.5 Hz, 3H); MS (APCI) m/z 387 (M+H)$^+$; Anal. calcd. for $C_{24}H_{26}N_4O$: C, 74.58; H, 6.78; N, 14.50. Found: C, 74.25; H, 6.61; N, 14.35.

Cytokine Induction in Human Cells

The compounds of Examples 1-18 have been found to modulate cytokine biosynthesis by inducing the production of interferon α and/or tumor necrosis factor α when tested using the method described below.

An in vitro human blood cell system is used to assess cytokine induction. Activity is based on the measurement of interferon and tumor necrosis factor (α) (IFN and TNF, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at 4×10⁶ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (30-0.014 µM). The final concentration of PBMC suspension is 2×10⁶ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay Interferon (α) and Tumor Necrosis Factor (α) Analysis by ELISA Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

Exemplary Compounds

Certain exemplary compounds have the Formula (IIa) and the following substituents, wherein each line of the table represents a specific compound. These compounds may be prepared using the synthetic methods described above.

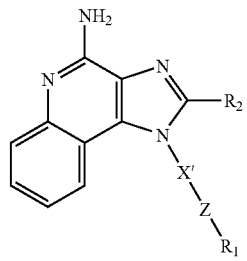

IIa

| X' | Z | $R_1$ | $R_2$ |
|---|---|---|---|
| —CH₂— | —C≡C— | phenyl | methyl |
| —CH₂— | —C≡C— | phenyl | propyl |
| —CH₂— | —C≡C— | phenyl | butyl |
| —CH₂— | —C≡C— | phenyl | ethoxymethyl |
| —CH₂— | —C≡C— | phenyl | 2-methoxyethyl |
| —CH₂— | —C≡C— | 4-chlorophenyl | methyl |
| —CH₂— | —C≡C— | 4-chlorophenyl | ethyl |
| —CH₂— | —C≡C— | 4-chlorophenyl | propyl |
| —CH₂— | —C≡C— | 4-chlorophenyl | butyl |
| —CH₂— | —C≡C— | 4-chlorophenyl | ethoxymethyl |
| —CH₂— | —C≡C— | 4-chlorophenyl | 2-methoxyethyl |
| —CH₂— | —C≡C— | 3-chlorophenyl | methyl |
| —CH₂— | —C≡C— | 3-chlorophenyl | ethyl |
| —CH₂— | —C≡C— | 3-chlorophenyl | propyl |
| —CH₂— | —C≡C— | 3-chlorophenyl | butyl |
| —CH₂— | —C≡C— | 3-chlorophenyl | ethoxymethyl |
| —CH₂— | —C≡C— | 3-chlorophenyl | 2-methoxyethyl |
| —CH₂— | —C≡C— | 4-fluorophenyl | methyl |
| —CH₂— | —C≡C— | 4-fluorophenyl | ethyl |
| —CH₂— | —C≡C— | 4-fluorophenyl | propyl |
| —CH₂— | —C≡C— | 4-fluorophenyl | butyl |
| —CH₂— | —C≡C— | 4-fluorophenyl | ethoxymethyl |
| —CH₂— | —C≡C— | 4-fluorophenyl | 2-methoxyethyl |
| —CH₂— | —C≡C— | 3-fluorophenyl | methyl |
| —CH₂— | —C≡C— | 3-fluorophenyl | ethyl |
| —CH₂— | —C≡C— | 3-fluorophenyl | propyl |
| —CH₂— | —C≡C— | 3-fluorophenyl | butyl |
| —CH₂— | —C≡C— | 3-fluorophenyl | ethoxymethyl |
| —CH₂— | —C≡C— | 3-fluorophenyl | 2-methoxyethyl |
| —CH₂— | —C≡C— | 4-methoxyphenyl | methyl |
| —CH₂— | —C≡C— | 4-methoxyphenyl | propyl |
| —CH₂— | —C≡C— | 4-methoxyphenyl | butyl |
| —CH₂— | —C≡C— | 4-methoxyphenyl | ethoxymethyl |
| —CH₂— | —C≡C— | 4-methoxyphenyl | 2-methoxyethyl |
| —CH₂— | —C≡C— | 3-methoxyphenyl | methyl |
| —CH₂— | —C≡C— | 3-methoxyphenyl | ethyl |
| —CH₂— | —C≡C— | 3-methoxyphenyl | propyl |
| —CH₂— | —C≡C— | 3-methoxyphenyl | butyl |
| —CH₂— | —C≡C— | 3-methoxyphenyl | ethoxymethyl |
| —CH₂— | —C≡C— | 3-methoxyphenyl | 2-methoxyethyl |
| —CH₂— | —C≡C— | 4-trifluoromethylphenyl | methyl |
| —CH₂— | —C≡C— | 4-trifluoromethylphenyl | ethyl |
| —CH₂— | —C≡C— | 4-trifluoromethylphenyl | propyl |
| —CH₂— | —C≡C— | 4-trifluoromethylphenyl | butyl |
| —CH₂— | —C≡C— | 4-trifluoromethylphenyl | ethoxymethyl |
| —CH₂— | —C≡C— | 4-trifluoromethylphenyl | 2-methoxyethyl |
| —CH₂— | —C≡C— | 3-trifluoromethylphenyl | methyl |
| —CH₂— | —C≡C— | 3-trifluoromethylphenyl | propyl |
| —CH₂— | —C≡C— | 3-trifluoromethylphenyl | butyl |
| —CH₂— | —C≡C— | 3-trifluoromethylphenyl | ethoxymethyl |
| —CH₂— | —C≡C— | 3-trifluoromethylphenyl | 2-methoxyethyl |
| —CH₂— | —C≡C— | 2-pyridinyl | methyl |
| —CH₂— | —C≡C— | 2-pyridinyl | ethyl |
| —CH₂— | —C≡C— | 2-pyridinyl | propyl |
| —CH₂— | —C≡C— | 2-pyridinyl | butyl |
| —CH₂— | —C≡C— | 2-pyridinyl | ethoxymethyl |
| —CH₂— | —C≡C— | 2-pyridinyl | 2-methoxyethyl |
| —CH₂— | —C≡C— | 3-pyridinyl | methyl |
| —CH₂— | —C≡C— | 3-pyridinyl | propyl |
| —CH₂— | —C≡C— | 3-pyridinyl | butyl |
| —CH₂— | —C≡C— | 3-pyridinyl | ethoxymethyl |
| —CH₂— | —C≡C— | 3-pyridinyl | 2-methoxyethyl |
| —CH₂— | —CH=CH— | phenyl | methyl |
| —CH₂— | —CH=CH— | phenyl | ethyl |
| —CH₂— | —CH=CH— | phenyl | propyl |

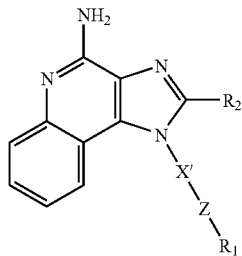

IIa

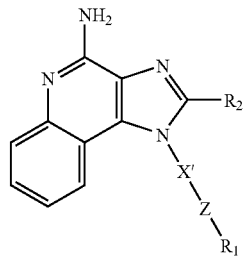

IIa

| X' | Z | R₁ | R₂ |
|---|---|---|---|
| —CH₂— | —CH=CH— | phenyl | butyl |
| —CH₂— | —CH=CH— | phenyl | ethoxymethyl |
| —CH₂— | —CH=CH— | phenyl | 2-methoxyethyl |
| —CH₂— | —CH=CH— | 4-chlorophenyl | methyl |
| —CH₂— | —CH=CH— | 4-chlorophenyl | ethyl |
| —CH₂— | —CH=CH— | 4-chlorophenyl | propyl |
| —CH₂— | —CH=CH— | 4-chlorophenyl | butyl |
| —CH₂— | —CH=CH— | 4-chlorophenyl | ethoxymethyl |
| —CH₂— | —CH=CH— | 4-chlorophenyl | 2-methoxyethyl |
| —CH₂— | —CH=CH— | 3-chlorophenyl | methyl |
| —CH₂— | —CH=CH— | 3-chlorophenyl | ethyl |
| —CH₂— | —CH=CH— | 3-chlorophenyl | propyl |
| —CH₂— | —CH=CH— | 3-chlorophenyl | butyl |
| —CH₂— | —CH=CH— | 3-chlorophenyl | ethoxymethyl |
| —CH₂— | —CH=CH— | 3-chlorophenyl | 2-methoxyethyl |
| —CH₂— | —CH=CH— | 4-fluorophenyl | methyl |
| —CH₂— | —CH=CH— | 4-fluorophenyl | ethyl |
| —CH₂— | —CH=CH— | 4-fluorophenyl | propyl |
| —CH₂— | —CH=CH— | 4-fluorophenyl | butyl |
| —CH₂— | —CH=CH— | 4-fluorophenyl | ethoxymethyl |
| —CH₂— | —CH=CH— | 4-fluorophenyl | 2-methoxyethyl |
| —CH₂— | —CH=CH— | 3-fluorophenyl | methyl |
| —CH₂— | —CH=CH— | 3-fluorophenyl | ethyl |
| —CH₂— | —CH=CH— | 3-fluorophenyl | propyl |
| —CH₂— | —CH=CH— | 3-fluorophenyl | butyl |
| —CH₂— | —CH=CH— | 3-fluorophenyl | ethoxymethyl |
| —CH₂— | —CH=CH— | 3-fluorophenyl | 2-methoxyethyl |
| —CH₂— | —CH=CH— | 4-methoxyphenyl | methyl |
| —CH₂— | —CH=CH— | 4-methoxyphenyl | ethyl |
| —CH₂— | —CH=CH— | 4-methoxyphenyl | propyl |
| —CH₂— | —CH=CH— | 4-methoxyphenyl | butyl |
| —CH₂— | —CH=CH— | 4-methoxyphenyl | ethoxymethyl |
| —CH₂— | —CH=CH— | 4-methoxyphenyl | 2-methoxyethyl |
| —CH₂— | —CH=CH— | 3-methoxyphenyl | methyl |
| —CH₂— | —CH=CH— | 3-methoxyphenyl | ethyl |
| —CH₂— | —CH=CH— | 3-methoxyphenyl | propyl |
| —CH₂— | —CH=CH— | 3-methoxyphenyl | butyl |
| —CH₂— | —CH=CH— | 3-methoxyphenyl | ethoxymethyl |
| —CH₂— | —CH=CH— | 3-methoxyphenyl | 2-methoxyethyl |
| —CH₂— | —CH=CH— | 4-trifluoromethylphenyl | methyl |
| —CH₂— | —CH=CH— | 4-trifluoromethylphenyl | ethyl |
| —CH₂— | —CH=CH— | 4-trifluoromethylphenyl | propyl |
| —CH₂— | —CH=CH— | 4-trifluoromethylphenyl | butyl |
| —CH₂— | —CH=CH— | 4-trifluoromethylphenyl | ethoxymethyl |
| —CH₂— | —CH=CH— | 4-trifluoromethylphenyl | 2-methoxyethyl |
| —CH₂— | —CH=CH— | 3-trifluoromethylphenyl | methyl |
| —CH₂— | —CH=CH— | 3-trifluoromethylphenyl | ethyl |
| —CH₂— | —CH=CH— | 3-trifluoromethylphenyl | propyl |
| —CH₂— | —CH=CH— | 3-trifluoromethylphenyl | butyl |
| —CH₂— | —CH=CH— | 3-trifluoromethylphenyl | ethoxymethyl |
| —CH₂— | —CH=CH— | 3-trifluoromethylphenyl | 2-methoxyethyl |
| —CH₂— | —CH=CH— | 2-pyridinyl | methyl |
| —CH₂— | —CH=CH— | 2-pyridinyl | ethyl |
| —CH₂— | —CH=CH— | 2-pyridinyl | propyl |
| —CH₂— | —CH=CH— | 2-pyridinyl | butyl |
| —CH₂— | —CH=CH— | 2-pyridinyl | ethoxymethyl |
| —CH₂— | —CH=CH— | 2-pyridinyl | 2-methoxyethyl |
| —CH₂— | —CH=CH— | 3-pyridinyl | methyl |
| —CH₂— | —CH=CH— | 3-pyridinyl | ethyl |
| —CH₂— | —CH=CH— | 3-pyridinyl | propyl |
| —CH₂— | —CH=CH— | 3-pyridinyl | butyl |
| —CH₂— | —CH=CH— | 3-pyridinyl | ethoxymethyl |
| —CH₂— | —CH=CH— | 3-pyridinyl | 2-methoxyethyl |

| X' | Z | R₁ | R₂ |
|---|---|---|---|
| —(CH₂)₂— | —C≡C— | phenyl | methyl |
| —(CH₂)₂— | —C≡C— | phenyl | ethyl |
| —(CH₂)₂— | —C≡C— | phenyl | propyl |
| —(CH₂)₂— | —C≡C— | phenyl | butyl |
| —(CH₂)₂— | —C≡C— | phenyl | ethoxymethyl |
| —(CH₂)₂— | —C≡C— | phenyl | 2-methoxyethyl |
| —(CH₂)₂— | —C≡C— | 4-chlorophenyl | methyl |
| —(CH₂)₂— | —C≡C— | 4-chlorophenyl | ethyl |
| —(CH₂)₂— | —C≡C— | 4-chlorophenyl | propyl |
| —(CH₂)₂— | —C≡C— | 4-chlorophenyl | butyl |
| —(CH₂)₂— | —C≡C— | 4-chlorophenyl | ethoxymethyl |
| —(CH₂)₂— | —C≡C— | 4-chlorophenyl | 2-methoxyethyl |
| —(CH₂)₂— | —C≡C— | 3-chlorophenyl | methyl |
| —(CH₂)₂— | —C≡C— | 3-chlorophenyl | ethyl |
| —(CH₂)₂— | —C≡C— | 3-chlorophenyl | propyl |
| —(CH₂)₂— | —C≡C— | 3-chlorophenyl | butyl |
| —(CH₂)₂— | —C≡C— | 3-chlorophenyl | ethoxymethyl |
| —(CH₂)₂— | —C≡C— | 3-chlorophenyl | 2-methoxyethyl |
| —(CH₂)₂— | —C≡C— | 4-fluorophenyl | methyl |
| —(CH₂)₂— | —C≡C— | 4-fluorophenyl | ethyl |
| —(CH₂)₂— | —C≡C— | 4-fluorophenyl | propyl |
| —(CH₂)₂— | —C≡C— | 4-fluorophenyl | butyl |
| —(CH₂)₂— | —C≡C— | 4-fluorophenyl | ethoxymethyl |
| —(CH₂)₂— | —C≡C— | 4-fluorophenyl | 2-methoxyethyl |
| —(CH₂)₂— | —C≡C— | 3-fluorophenyl | methyl |
| —(CH₂)₂— | —C≡C— | 3-fluorophenyl | ethyl |
| —(CH₂)₂— | —C≡C— | 3-fluorophenyl | propyl |
| —(CH₂)₂— | —C≡C— | 3-fluorophenyl | butyl |
| —(CH₂)₂— | —C≡C— | 3-fluorophenyl | ethoxymethyl |
| —(CH₂)₂— | —C≡C— | 3-fluorophenyl | 2-methoxyethyl |
| —(CH₂)₂— | —C≡C— | 4-methoxyphenyl | methyl |
| —(CH₂)₂— | —C≡C— | 4-methoxyphenyl | ethyl |
| —(CH₂)₂— | —C≡C— | 4-methoxyphenyl | propyl |
| —(CH₂)₂— | —C≡C— | 4-methoxyphenyl | butyl |
| —(CH₂)₂— | —C≡C— | 4-methoxyphenyl | ethoxymethyl |
| —(CH₂)₂— | —C≡C— | 4-methoxyphenyl | 2-methoxyethyl |
| —(CH₂)₂— | —C≡C— | 3-methoxyphenyl | methyl |
| —(CH₂)₂— | —C≡C— | 3-methoxyphenyl | ethyl |
| —(CH₂)₂— | —C≡C— | 3-methoxyphenyl | propyl |
| —(CH₂)₂— | —C≡C— | 3-methoxyphenyl | butyl |
| —(CH₂)₂— | —C≡C— | 3-methoxyphenyl | ethoxymethyl |
| —(CH₂)₂— | —C≡C— | 3-methoxyphenyl | 2-methoxyethyl |
| —(CH₂)₂— | —C≡C— | 4-trifluoromethylphenyl | methyl |
| —(CH₂)₂— | —C≡C— | 4-trifluoromethylphenyl | ethyl |
| —(CH₂)₂— | —C≡C— | 4-trifluoromethylphenyl | propyl |
| —(CH₂)₂— | —C≡C— | 4-trifluoromethylphenyl | butyl |
| —(CH₂)₂— | —C≡C— | 4-trifluoromethylphenyl | ethoxymethyl |
| —(CH₂)₂— | —C≡C— | 4-trifluoromethylphenyl | 2-methoxyethyl |
| —(CH₂)₂— | —C≡C— | 3-trifluoromethylphenyl | methyl |
| —(CH₂)₂— | —C≡C— | 3-trifluoromethylphenyl | ethyl |
| —(CH₂)₂— | —C≡C— | 3-trifluoromethylphenyl | propyl |
| —(CH₂)₂— | —C≡C— | 3-trifluoromethylphenyl | butyl |
| —(CH₂)₂— | —C≡C— | 3-trifluoromethylphenyl | ethoxymethyl |
| —(CH₂)₂— | —C≡C— | 3-trifluoromethylphenyl | 2-methoxyethyl |
| —(CH₂)₂— | —C≡C— | 2-pyridinyl | methyl |
| —(CH₂)₂— | —C≡C— | 2-pyridinyl | ethyl |
| —(CH₂)₂— | —C≡C— | 2-pyridinyl | propyl |
| —(CH₂)₂— | —C≡C— | 2-pyridinyl | butyl |
| —(CH₂)₂— | —C≡C— | 2-pyridinyl | ethoxymethyl |
| —(CH₂)₂— | —C≡C— | 2-pyridinyl | 2-methoxyethyl |
| —(CH₂)₂— | —C≡C— | 3-pyridinyl | methyl |
| —(CH₂)₂— | —C≡C— | 3-pyridinyl | ethyl |
| —(CH₂)₂— | —C≡C— | 3-pyridinyl | propyl |

-continued

IIa

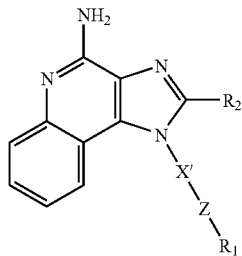

| X' | Z | R₁ | R₂ |
|---|---|---|---|
| —(CH₂)₂— | —C≡C— | 3-pyridinyl | butyl |
| —(CH₂)₂— | —C≡C— | 3-pyridinyl | ethoxymethyl |
| —(CH₂)₂— | —C≡C— | 3-pyridinyl | 2-methoxyethyl |
| —(CH₂)₂— | —CH=CH— | phenyl | methyl |
| —(CH₂)₂— | —CH=CH— | phenyl | ethyl |
| —(CH₂)₂— | —CH=CH— | phenyl | propyl |
| —(CH₂)₂— | —CH=CH— | phenyl | butyl |
| —(CH₂)₂— | —CH=CH— | phenyl | ethoxymethyl |
| —(CH₂)₂— | —CH=CH— | phenyl | 2-methoxyethyl |
| —(CH₂)₂— | —CH=CH— | 4-chlorophenyl | methyl |
| —(CH₂)₂— | —CH=CH— | 4-chlorophenyl | ethyl |
| —(CH₂)₂— | —CH=CH— | 4-chlorophenyl | propyl |
| —(CH₂)₂— | —CH=CH— | 4-chlorophenyl | butyl |
| —(CH₂)₂— | —CH=CH— | 4-chlorophenyl | ethoxymethyl |
| —(CH₂)₂— | —CH=CH— | 4-chlorophenyl | 2-methoxyethyl |
| —(CH₂)₂— | —CH=CH— | 3-chlorophenyl | methyl |
| —(CH₂)₂— | —CH=CH— | 3-chlorophenyl | ethyl |
| —(CH₂)₂— | —CH=CH— | 3-chlorophenyl | propyl |
| —(CH₂)₂— | —CH=CH— | 3-chlorophenyl | butyl |
| —(CH₂)₂— | —CH=CH— | 3-chlorophenyl | ethoxymethyl |
| —(CH₂)₂— | —CH=CH— | 3-chlorophenyl | 2-methoxyethyl |
| —(CH₂)₂— | —CH=CH— | 4-fluorophenyl | methyl |
| —(CH₂)₂— | —CH=CH— | 4-fluorophenyl | ethyl |
| —(CH₂)₂— | —CH=CH— | 4-fluorophenyl | propyl |
| —(CH₂)₂— | —CH=CH— | 4-fluorophenyl | butyl |
| —(CH₂)₂— | —CH=CH— | 4-fluorophenyl | ethoxymethyl |
| —(CH₂)₂— | —CH=CH— | 4-fluorophenyl | 2-methoxyethyl |
| —(CH₂)₂— | —CH=CH— | 3-fluorophenyl | methyl |
| —(CH₂)₂— | —CH=CH— | 3-fluorophenyl | ethyl |
| —(CH₂)₂— | —CH=CH— | 3-fluorophenyl | propyl |
| —(CH₂)₂— | —CH=CH— | 3-fluorophenyl | butyl |
| —(CH₂)₂— | —CH=CH— | 3-fluorophenyl | ethoxymethyl |
| —(CH₂)₂— | —CH=CH— | 3-fluorophenyl | 2-methoxyethyl |
| —(CH₂)₂— | —CH=CH— | 4-methoxyphenyl | methyl |
| —(CH₂)₂— | —CH=CH— | 4-methoxyphenyl | ethyl |
| —(CH₂)₂— | —CH=CH— | 4-methoxyphenyl | propyl |
| —(CH₂)₂— | —CH=CH— | 4-methoxyphenyl | butyl |
| —(CH₂)₂— | —CH=CH— | 4-methoxyphenyl | ethoxymethyl |
| —(CH₂)₂— | —CH=CH— | 4-methoxyphenyl | 2-methoxyethyl |
| —(CH₂)₂— | —CH=CH— | 3-methoxyphenyl | methyl |
| —(CH₂)₂— | —CH=CH— | 3-methoxyphenyl | ethyl |
| —(CH₂)₂— | —CH=CH— | 3-methoxyphenyl | propyl |
| —(CH₂)₂— | —CH=CH— | 3-methoxyphenyl | butyl |
| —(CH₂)₂— | —CH=CH— | 3-methoxyphenyl | ethoxymethyl |
| —(CH₂)₂— | —CH=CH— | 3-methoxyphenyl | 2-methoxyethyl |
| —(CH₂)₂— | —CH=CH— | 4-trifluoromethylphenyl | methyl |
| —(CH₂)₂— | —CH=CH— | 4-trifluoromethylphenyl | ethyl |
| —(CH₂)₂— | —CH=CH— | 4-trifluoromethylphenyl | propyl |
| —(CH₂)₂— | —CH=CH— | 4-trifluoromethylphenyl | butyl |
| —(CH₂)₂— | —CH=CH— | 4-trifluoromethylphenyl | ethoxymethyl |
| —(CH₂)₂— | —CH=CH— | 4-trifluoromethylphenyl | 2-methoxyethyl |
| —(CH₂)₂— | —CH=CH— | 3-trifluoromethylphenyl | methyl |
| —(CH₂)₂— | —CH=CH— | 3-trifluoromethylphenyl | ethyl |
| —(CH₂)₂— | —CH=CH— | 3-trifluoromethylphenyl | propyl |
| —(CH₂)₂— | —CH=CH— | 3-trifluoromethylphenyl | butyl |
| —(CH₂)₂— | —CH=CH— | 3-trifluoromethylphenyl | ethoxymethyl |
| —(CH₂)₂— | —CH=CH— | 3-trifluoromethylphenyl | 2-methoxyethyl |
| —(CH₂)₂— | —CH=CH— | 2-pyridinyl | methyl |
| —(CH₂)₂— | —CH=CH— | 2-pyridinyl | ethyl |
| —(CH₂)₂— | —CH=CH— | 2-pyridinyl | propyl |
| —(CH₂)₂— | —CH=CH— | 2-pyridinyl | butyl |
| —(CH₂)₂— | —CH=CH— | 2-pyridinyl | ethoxymethyl |
| —(CH₂)₂— | —CH=CH— | 2-pyridinyl | 2-methoxyethyl |
| —(CH₂)₂— | —CH=CH— | 3-pyridinyl | methyl |
| —(CH₂)₂— | —CH=CH— | 3-pyridinyl | ethyl |
| —(CH₂)₂— | —CH=CH— | 3-pyridinyl | propyl |
| —(CH₂)₂— | —CH=CH— | 3-pyridinyl | butyl |
| —(CH₂)₂— | —CH=CH— | 3-pyridinyl | ethoxymethyl |
| —(CH₂)₂— | —CH=CH— | 3-pyridinyl | 2-methoxyethyl |
| —(CH₂)₃— | —C≡C— | phenyl | methyl |
| —(CH₂)₃— | —C≡C— | phenyl | propyl |
| —(CH₂)₃— | —C≡C— | phenyl | butyl |
| —(CH₂)₃— | —C≡C— | phenyl | ethoxymethyl |
| —(CH₂)₃— | —C≡C— | phenyl | 2-methoxyethyl |
| —(CH₂)₃— | —C≡C— | 4-chlorophenyl | methyl |
| —(CH₂)₃— | —C≡C— | 4-chlorophenyl | ethyl |
| —(CH₂)₃— | —C≡C— | 4-chlorophenyl | propyl |
| —(CH₂)₃— | —C≡C— | 4-chlorophenyl | butyl |
| —(CH₂)₃— | —C≡C— | 4-chlorophenyl | ethoxymethyl |
| —(CH₂)₃— | —C≡C— | 4-chlorophenyl | 2-methoxyethyl |
| —(CH₂)₃— | —C≡C— | 3-chlorophenyl | methyl |
| —(CH₂)₃— | —C≡C— | 3-chlorophenyl | ethyl |
| —(CH₂)₃— | —C≡C— | 3-chlorophenyl | propyl |
| —(CH₂)₃— | —C≡C— | 3-chlorophenyl | butyl |
| —(CH₂)₃— | —C≡C— | 3-chlorophenyl | ethoxymethyl |
| —(CH₂)₃— | —C≡C— | 3-chlorophenyl | 2-methoxyethyl |
| —(CH₂)₃— | —C≡C— | 4-fluorophenyl | methyl |
| —(CH₂)₃— | —C≡C— | 4-fluorophenyl | ethyl |
| —(CH₂)₃— | —C≡C— | 4-fluorophenyl | propyl |
| —(CH₂)₃— | —C≡C— | 4-fluorophenyl | butyl |
| —(CH₂)₃— | —C≡C— | 4-fluorophenyl | ethoxymethyl |
| —(CH₂)₃— | —C≡C— | 4-fluorophenyl | 2-methoxyethyl |
| —(CH₂)₃— | —C≡C— | 3-fluorophenyl | methyl |
| —(CH₂)₃— | —C≡C— | 3-fluorophenyl | ethyl |
| —(CH₂)₃— | —C≡C— | 3-fluorophenyl | propyl |
| —(CH₂)₃— | —C≡C— | 3-fluorophenyl | butyl |
| —(CH₂)₃— | —C≡C— | 3-fluorophenyl | ethoxymethyl |
| —(CH₂)₃— | —C≡C— | 3-fluorophenyl | 2-methoxyethyl |
| —(CH₂)₃— | —C≡C— | 4-methoxyphenyl | methyl |
| —(CH₂)₃— | —C≡C— | 4-methoxyphenyl | propyl |
| —(CH₂)₃— | —C≡C— | 4-methoxyphenyl | butyl |
| —(CH₂)₃— | —C≡C— | 4-methoxyphenyl | ethoxymethyl |
| —(CH₂)₃— | —C≡C— | 4-methoxyphenyl | 2-methoxyethyl |
| —(CH₂)₃— | —C≡C— | 3-methoxyphenyl | methyl |
| —(CH₂)₃— | —C≡C— | 3-methoxyphenyl | ethyl |
| —(CH₂)₃— | —C≡C— | 3-methoxyphenyl | propyl |
| —(CH₂)₃— | —C≡C— | 3-methoxyphenyl | butyl |
| —(CH₂)₃— | —C≡C— | 3-methoxyphenyl | ethoxymethyl |
| —(CH₂)₃— | —C≡C— | 3-methoxyphenyl | 2-methoxyethyl |
| —(CH₂)₃— | —C≡C— | 4-trifluoromethylphenyl | methyl |
| —(CH₂)₃— | —C≡C— | 4-trifluoromethylphenyl | ethyl |
| —(CH₂)₃— | —C≡C— | 4-trifluoromethylphenyl | propyl |
| —(CH₂)₃— | —C≡C— | 4-trifluoromethylphenyl | butyl |
| —(CH₂)₃— | —C≡C— | 4-trifluoromethylphenyl | ethoxymethyl |
| —(CH₂)₃— | —C≡C— | 4-trifluoromethylphenyl | 2-methoxyethyl |
| —(CH₂)₃— | —C≡C— | 3-trifluoromethylphenyl | methyl |
| —(CH₂)₃— | —C≡C— | 3-trifluoromethylphenyl | propyl |
| —(CH₂)₃— | —C≡C— | 3-trifluoromethylphenyl | butyl |
| —(CH₂)₃— | —C≡C— | 3-trifluoromethylphenyl | ethoxymethyl |
| —(CH₂)₃— | —C≡C— | 3-trifluoromethylphenyl | 2-methoxyethyl |
| —(CH₂)₃— | —C≡C— | 2-pyridinyl | methyl |
| —(CH₂)₃— | —C≡C— | 2-pyridinyl | ethyl |
| —(CH₂)₃— | —C≡C— | 2-pyridinyl | propyl |
| —(CH₂)₃— | —C≡C— | 2-pyridinyl | butyl |
| —(CH₂)₃— | —C≡C— | 2-pyridinyl | ethoxymethyl |
| —(CH₂)₃— | —C≡C— | 2-pyridinyl | 2-methoxyethyl |

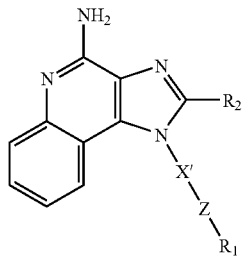

IIa

| X' | Z | R₁ | R₂ |
|---|---|---|---|
| —(CH₂)₃— | —C≡C— | 3-pyridinyl | methyl |
| —(CH₂)₃— | —C≡C— | 3-pyridinyl | propyl |
| —(CH₂)₃— | —C≡C— | 3-pyridinyl | butyl |
| —(CH₂)₃— | —C≡C— | 3-pyridinyl | ethoxymethyl |
| —(CH₂)₃— | —C≡C— | 3-pyridinyl | 2-methoxyethyl |
| —(CH₂)₃— | —CH=CH— | phenyl | methyl |
| —(CH₂)₃— | —CH=CH— | phenyl | ethyl |
| —(CH₂)₃— | —CH=CH— | phenyl | propyl |
| —(CH₂)₃— | —CH=CH— | phenyl | butyl |
| —(CH₂)₃— | —CH=CH— | phenyl | ethoxymethyl |
| —(CH₂)₃— | —CH=CH— | phenyl | 2-methoxyethyl |
| —(CH₂)₃— | —CH=CH— | 4-chlorophenyl | methyl |
| —(CH₂)₃— | —CH=CH— | 4-chlorophenyl | ethyl |
| —(CH₂)₃— | —CH=CH— | 4-chlorophenyl | propyl |
| —(CH₂)₃— | —CH=CH— | 4-chlorophenyl | butyl |
| —(CH₂)₃— | —CH=CH— | 4-chlorophenyl | ethoxymethyl |
| —(CH₂)₃— | —CH=CH— | 4-chlorophenyl | 2-methoxyethyl |
| —(CH₂)₃— | —CH=CH— | 3-chlorophenyl | methyl |
| —(CH₂)₃— | —CH=CH— | 3-chlorophenyl | ethyl |
| —(CH₂)₃— | —CH=CH— | 3-chlorophenyl | propyl |
| —(CH₂)₃— | —CH=CH— | 3-chlorophenyl | butyl |
| —(CH₂)₃— | —CH=CH— | 3-chlorophenyl | ethoxymethyl |
| —(CH₂)₃— | —CH=CH— | 3-chlorophenyl | 2-methoxyethyl |
| —(CH₂)₃— | —CH=CH— | 4-fluorophenyl | methyl |
| —(CH₂)₃— | —CH=CH— | 4-fluorophenyl | ethyl |
| —(CH₂)₃— | —CH=CH— | 4-fluorophenyl | propyl |
| —(CH₂)₃— | —CH=CH— | 4-fluorophenyl | butyl |
| —(CH₂)₃— | —CH=CH— | 4-fluorophenyl | ethoxymethyl |
| —(CH₂)₃— | —CH=CH— | 4-fluorophenyl | 2-methoxyethyl |
| —(CH₂)₃— | —CH=CH— | 3-fluorophenyl | methyl |
| —(CH₂)₃— | —CH=CH— | 3-fluorophenyl | ethyl |
| —(CH₂)₃— | —CH=CH— | 3-fluorophenyl | propyl |
| —(CH₂)₃— | —CH=CH— | 3-fluorophenyl | butyl |
| —(CH₂)₃— | —CH=CH— | 3-fluorophenyl | ethoxymethyl |
| —(CH₂)₃— | —CH=CH— | 3-fluorophenyl | 2-methoxyethyl |
| —(CH₂)₃— | —CH=CH— | 4-methoxyphenyl | methyl |
| —(CH₂)₃— | —CH=CH— | 4-methoxyphenyl | ethyl |
| —(CH₂)₃— | —CH=CH— | 4-methoxyphenyl | propyl |
| —(CH₂)₃— | —CH=CH— | 4-methoxyphenyl | butyl |
| —(CH₂)₃— | —CH=CH— | 4-methoxyphenyl | ethoxymethyl |
| —(CH₂)₃— | —CH=CH— | 4-methoxyphenyl | 2-methoxyethyl |
| —(CH₂)₃— | —CH=CH— | 3-methoxyphenyl | methyl |
| —(CH₂)₃— | —CH=CH— | 3-methoxyphenyl | ethyl |
| —(CH₂)₃— | —CH=CH— | 3-methoxyphenyl | propyl |
| —(CH₂)₃— | —CH=CH— | 3-methoxyphenyl | butyl |
| —(CH₂)₃— | —CH=CH— | 3-methoxyphenyl | ethoxymethyl |
| —(CH₂)₃— | —CH=CH— | 3-methoxyphenyl | 2-methoxyethyl |
| —(CH₂)₃— | —CH=CH— | 4-trifluoromethylphenyl | methyl |
| —(CH₂)₃— | —CH=CH— | 4-trifluoromethylphenyl | ethyl |
| —(CH₂)₃— | —CH=CH— | 4-trifluoromethylphenyl | propyl |
| —(CH₂)₃— | —CH=CH— | 4-trifluoromethylphenyl | butyl |
| —(CH₂)₃— | —CH=CH— | 4-trifluoromethylphenyl | ethoxymethyl |
| —(CH₂)₃— | —CH=CH— | 4-trifluoromethylphenyl | 2-methoxyethyl |
| —(CH₂)₃— | —CH=CH— | 3-trifluoromethylphenyl | methyl |
| —(CH₂)₃— | —CH=CH— | 3-trifluoromethylphenyl | ethyl |
| —(CH₂)₃— | —CH=CH— | 3-trifluoromethylphenyl | propyl |
| —(CH₂)₃— | —CH=CH— | 3-trifluoromethylphenyl | butyl |
| —(CH₂)₃— | —CH=CH— | 3-trifluoromethylphenyl | ethoxymethyl |
| —(CH₂)₃— | —CH=CH— | 3-trifluoromethylphenyl | 2-methoxyethyl |
| —(CH₂)₃— | —CH=CH— | 2-pyridinyl | methyl |
| —(CH₂)₃— | —CH=CH— | 2-pyridinyl | ethyl |
| —(CH₂)₃— | —CH=CH— | 2-pyridinyl | propyl |
| —(CH₂)₃— | —CH=CH— | 2-pyridinyl | butyl |
| —(CH₂)₃— | —CH=CH— | 2-pyridinyl | ethoxymethyl |

IIa

| X' | Z | R₁ | R₂ |
|---|---|---|---|
| —(CH₂)₃— | —CH=CH— | 2-pyridinyl | 2-methoxyethyl |
| —(CH₂)₃— | —CH=CH— | 3-pyridinyl | methyl |
| —(CH₂)₃— | —CH=CH— | 3-pyridinyl | propyl |
| —(CH₂)₃— | —CH=CH— | 3-pyridinyl | butyl |
| —(CH₂)₃— | —CH=CH— | 3-pyridinyl | ethoxymethyl |
| —(CH₂)₃— | —CH=CH— | 3-pyridinyl | 2-methoxyethyl |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the formula (II):

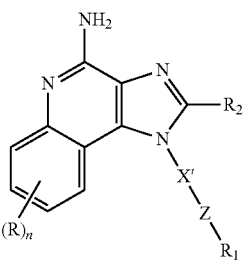

(II)

wherein:
Z is —C≡C—;
X' is —CH(R₃)—;
R₁ is selected from the group consisting of:
—Ar and
—Ar'—Y—R₄;
Ar is phenyl which can be unsubstituted or can be substituted by one or more substituents independently selected from the group consisting of alkyl, alkoxy, haloalkyl, haloalkoxy, halogen, nitro, hydroxy, hydroxyalkyl, mercapto, cyano, carboxy, formyl, amino, alkylamino, and dialkylamino;
Ar' is phenylene;
R₂ is selected from the group consisting of hydrogen and alkyl, wherein the alkyl group can be unsubstituted or substituted by one or more substituents independently selected from the group consisting of alkyl and alkoxy;
Y is selected from the group consisting of:
—C(R₆)—, —C(R$_6$)—O—,
—O—C(R$_6$)—, and
—O—C(O)—O—;

R$_3$ is hydrogen or C$_{1-10}$ alkyl;

R$_4$ is selected from the group consisting of hydrogen, alkyl, and alkenyl;

R$_6$ is =O; and n is 0;

or a pharmaceutically acceptable salt thereof.

2. The compound or salt of claim 1 wherein R$_2$ is hydrogen, alkyl, or alkoxyalkylenyl.

3. The compound or salt of claim 2 wherein R$_2$ is methyl, ethyl, propyl, butyl, 2-methoxyethyl, or ethoxymethyl.

4. The compound or salt of claim 1 wherein X' is —CH$_2$—.

5. The compound or salt of claim 1 wherein R$_1$ is —Ar.

6. The compound or salt of claim 5 wherein R$_1$ is phenyl wherein the phenyl group can be unsubstituted or substituted by alkoxy, haloalkyl, halogen, nitro, or cyano.

7. The compound or salt of claim 6 wherein R$_1$ is phenyl, 3-chlorophenyl, 4-chlorophenyl, 3-fluorophenyl, 4-fluorophenyl, 3-methoxyphenyl, 4-methoxyphenyl, 3-trifluoromethylphenyl, or 4-trifluoromethylphenyl.

8. A pharmaceutical composition comprising a therapeutically effective amount of a compound or salt of claim 1 in combination with a pharmaceutically acceptable carrier.

9. The compound or salt of claim 1, wherein the compound is 4-[3-(4-amino-2-ethyl-1H-imidazo[4,5-c]quinolin-1-yl)-1-propynyl]benzonitrile.

10. The compound or salt of claim 1, wherein the compound is 2-ethyl-1-(3-phenyl-2-propynyl)-1H-imidazo[4,5-c]quinolin-4-amine.

11. The compound or salt of claim 1, wherein the compound is ethyl 4-[3-(4-Amino-2-ethyl-1H-imidazo[4,5-c]quinolin-1-yl)-1-propynyl]benzoate.

12. The compound or salt of claim 1, wherein the compound is 2-ethyl-1-[3-(4-methoxyphenyl)-2-propynyl]-1H-imidazo[4,5-c]quinolin-4-amine.

13. The compound or salt of claim 1, wherein the compound is 2-ethyl-1-[3-(3-trifluoromethylphenyl)-2-propynyl]-1H-imidazo[4,5-c]quinolin-4-amine.

14. The compound or salt of claim 1, wherein the compound is 2-ethyl-1-[3-(2-trifluoromethylphenyl)-2-propynyl]-1H-imidazo[4,5-c]quinolin-4-amine.

15. The compound or salt of claim 1, wherein the compound is 2-ethyl-1-[3-(4-nitrophenyl)-2-propynyl]-1H-imidazo[4,5-c]quinolin-4-amine or 2-ethyl-1-[3-(3-nitrophenyl)-2-propynyl]-1H-imidazo[4,5-c]quinolin-4-amine.

* * * * *